(12) United States Patent
Wolven et al.

(10) Patent No.: US 6,448,041 B1
(45) Date of Patent: Sep. 10, 2002

(54) COLON CANCER MARKER

(75) Inventors: Amy K. Wolven, Oakland; Randi E. Krasnow, Stanford; Bridget A. Warren, Cupertino; Mariah R. Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/740,235

(22) Filed: Dec. 18, 2000

(51) Int. Cl.[7] .................... C12P 2/06; C12P 21/04; C12N 15/00; C12N 15/09; C12N 15/63; C12N 15/74; C12N 5/00; C12N 5/02; C07H 21/02; C07H 21/04

(52) U.S. Cl. .................. 435/69.1; 435/70.1; 435/320.1; 435/325; 536/23.1; 536/23.5

(58) Field of Search ................. 536/23.1, 23.5; 435/320.1, 70.1, 69.1, 325

(56) References Cited

PUBLICATIONS

Alberts et al., Molecular Biology of the Cell, 3rd edition, 1994, p. 465.*
Potter, JD., "Colorectal Cancer: Molecules and Populations", J. Natl Cancer Institute 91: 916–932 (1999).
National Institutes of Health, DHHS Publ No. (NIH) 90–2789) Ries et al., (1990) (Abstract).
El–Deiry et al., "High expression of the DNA methyltransferase gene characterizes human neoplastic cells and progression stages of colon cancer", Proc Natl Acad Sci USA 88:3470–3474 (1991).
Antequera et al., "High Levels of De Novo Methylation and Altered Chromatin Structure at CpG Islands in Cell Lines", Cell 62: 503–514 (1990).
Issa, J–P J et al., "Methylation of the oestrogen receptor CpG island links ageing and neoplasia in human colon", Nature Genetics 7:536–540 (1994).
Platet et al., "Unliganded and Liganded Estrogen Receptors Protect against Cancer Invasion via Different Mechanisms", Mol Endocrinol 14:999–1009 (2000).
Stenmark and Aasland, "FYVE–finger proteins –effectors of an inositol lipid", J. Cell Science 112: 4175–4183 (1999).
Komada and Soriano, "Hrs, a FYVE finger protein localized to early endosomes, is implicated in vesicular traffic and required for ventral folding morphogenesis", Genes Dev 13:1475–1485 (1999).
Dove et al., "The intestinal epithelium and its neoplasma: genetic, cellular and tissue interactions", Phil Trans R Soc Lond B 353: 915–923 (1998).
Boll et al., "Messenger RNA's Expressed in Intestine of Adult but Not Baby Rabbits", J. Biol Chem 268:12901–12911 (1993).

* cited by examiner

*Primary Examiner*—Geetha P. Bansal
*Assistant Examiner*—Natalie Davis
(74) *Attorney, Agent, or Firm*—Incyte Genomics, Inc.

(57) ABSTRACT

The invention provides a cDNA which encodes a colon cancer marker. It also provides for the use of the cDNA, fragments, complements, and variants thereof and of the encoded protein, portions thereof and antibodies thereto for diagnosis and treatment of colon disorders, particularly colon cancer and polyps. The invention additionally provides expression vectors and host cells for the production of the protein and a transgenic model system.

10 Claims, 22 Drawing Sheets

```
5'
     9                  18            27            36            45            54
GCC TGC CGA       GTT CCG AGC   GAC CGA TGG   AGA TGG CGG   CTG CGG CTG   AGT GAC GGA
    63                 72            81            90            99           108
CGG TGG AGG       CCC AGA GCC   CGG GCC TGA   AGG GGG CAA   ACC TGG GTG   CCC GCA
   117                126           135           144           153           162
GGA GCC CGG       CAG GGT GTC   TTA CAA TCA   AGA ACT TAC   TAT ATG TGG   TTG AAT
   171                180           189           198           207           216
AAA CAA TCA       AGG TAA AGA   GCA TCA AGT   TTC AAA AAC   TGC TTG ATA   AGT ACT
   225                234           243           252           261           270
TCA GAC ATT       CCC CCA GTG   GCT GAA TAT   GCA TTA TGA   TTA AGT TGG   ATC ATT
   279                288           297           306           315           324
TCA TCC CCA       AGA ATT GCC   AAG GGC TCC   TCC TAC TCC   AGA GAG GAA   ACC
   333                342           351           360           369           378
TGG AAT GAA       TGT AAG CCA   CTT CAC CAT   CTG TGT GCT   TAA GCT AAT
   387                396           405           414           423           432
TCA TCC AGG       GCC ATG CCT   TGG GAG GAA   TCA AGC TGA   CTC TTG GCA   TGA GAT
GCT GCG GGA       ACC ATG GTT
```

FIGURE 1A

```
              441             450             459             468             477             486
         TCC TGC CTT CCT AGG GAG AGC ACT GCC ATG GCT TCT CTG GAC GAC CCA
                                              M   A   S   L   D   D   P 495             504             513             522             531             540
         GGG GAA GTG AGG GAG TTC CTC TGC CCT CTG TGC CTG AAG GAT CTG CAG TCT
          G   E   V   R   E   F   L   C   P   L   C   L   K   D   L   Q   S 549             558             567             576             585             594
         TTC TAT CAG CTT CAC TCA CAT TAC TGC GAA GAA CAC TCA GGG GAA GAC CGT GAT
          F   Y   Q   L   H   S   H   Y   C   E   E   H   S   G   E   D   R   D 603             612             621             630             639             648
         GTC AAA GGG CAA ATT AAA AGT CTT GTC CAG AAG GCT AAA AAA GCA AAG GAC AGG
          V   K   G   Q   I   K   S   L   V   Q   K   A   K   K   A   K   D   R 657             666             675             684             693             702
         TTG TTG AAA CGA GAA GGG GAT GAT CGA GCA GAG TCA GGG ACC CAA GGA TAT GAG
          L   L   K   R   E   G   D   D   R   A   E   S   G   T   Q   G   Y   E
```

FIGURE 1B

```
       711         720         729         738         747         756
TCT TTC AGC TAT GGA GTT GAT CCT TAC ATG TGG GAA CCC CAG GAG CTT GGT
 S   F   S   Y   G   V   D   P   Y   M   W   E   P   Q   E   L   G 765         774         783         792         801         810
GCT GTG AGA AGC CAT CTT TCC GAC TTC AAA AAA CAC CGA GCT AGA ATT GAC
 A   V   R   S   H   L   S   D   F   K   K   H   R   A   R   I   D 819         828         837         846         855         864
CAC TAT GTT GTG GAA ACT AAT AAA CTA ATA AGG TTA GAG AAG CTC ACT GCA
 H   Y   V   V   E   T   N   K   L   I   R   L   E   K   L   T   A 873         882         891         900         909         918
TTT GAC AGA ACA AAT ACT GAG TCT GCA AAG ATT CGA GCA ATA GAA AAG TCT GTG
 F   D   R   T   N   T   E   S   A   K   I   R   A   I   E   K   S   V 927         936         945         954         963         972
GTG CCT TGG GTC AAC GAC CAG GAT TCT GCA GTC CCT TTC TGT CCA GAC TGT GGG AAT AAG
 V   P   W   V   N   D   Q   D   S   A   V   P   F   C   P   D   C   G   N   K
```

FIGURE 1C

FIGURE 1D

```
 981                990        999       1008       1017       1026
 TTC AGC ATC --- CGG AAC CGC --- CAC CAC TGC --- CGC CTC TGC --- GGG TCT ATT --- ATG TGC
  F   S   I  ---  R   N   R  ---  H   H   C  ---  R   L   C  ---  G   S   I  ---  M   C 1035               1044       1053       1062       1071       1080
 AAG AAG TGT --- ATG GAG CTC --- ATC AGC CTT --- CCC TTG GCA --- AAC AAG ACC --- AGT GCC
  K   K   C  ---  M   E   L  ---  I   S   L  ---  P   L   A  ---  N   K   T  ---  S   A 1089               1098       1107       1116       1125       1134
 AGC AAG GAG --- TCC CTG AGC --- ACC CAC AGC --- CAG CCC AGC --- TCA CCC AAC --- AGT GTC
  S   K   E  ---  S   L   S  ---  T   H   S  ---  Q   P   S  ---  S   P   N  ---  S   V 1143               1152       1161       1170       1179       1188
 CAT GGC TCC --- CGC CGA GGC --- AGC ATC AGC --- AGC ATG AGC --- AGC AGT GTC --- TCG GTC CTG
  H   G   S  ---  R   R   G  ---  S   I   S  ---  S   M   S  ---  S   S   V  ---  S   V   L 1197               1206       1215       1224       1233       1242
 GAT GAG AAG --- GAC GAT GAC --- CGG ATC CGC --- TGC TGT ACA --- CAC TGC AAG --- GAC ACG CTG
  D   E   K  ---  D   D   D  ---  R   I   R  ---  C   C   T  ---  H   C   K  ---  D   T   L
```

```
      1251            1260            1269            1278            1287            1296
CTC AAG AGA GAG CAG CAG ATT GAT GAG AAG GAG CAC ACA CCT GAC ATC GTG AAG
 L   K   R   E   Q   Q   I   D   E   K   E   H   T   P   D   I   V   K 1305            1314            1323            1332            1341            1350
CTC TAC GAG AAA TTA CGA CTT TGC ATG GAG AAA GTT GAC CAG AAA GCT CCA GAA
 L   Y   E   K   L   R   L   C   M   E   K   V   D   Q   K   A   P   E 1359            1368            1377            1386            1395            1404
TAC ATC AGG ATG GCA GCA TCA TTA AAT GCT GGG GAG ACA ACC TAC AGT CTG GAA
 Y   I   R   M   A   A   S   L   N   A   G   E   T   T   Y   S   L   E 1413            1422            1431            1440            1449            1458
CAT GCC AGT GAC CTT CGA GTG GAA GTG CAG AAA TAC GAG TAT GAG CTG ATA GAC GCT
 H   A   S   D   L   R   V   E   V   Q   K   Y   E   Y   E   L   I   D   A 1467            1476            1485            1494            1503            1512
TTA AGT AAG AAG ATC TTA ACC TTG GGC TTG AAC CAG GAC CCT CCA CCA CAT CCA
 L   S   K   K   I   L   T   L   G   L   N   Q   D   P   P   P   H   P
```

FIGURE 1E

```
        1521            1530            1539            1548            1557            1566
AGC AAT TTG CGG CTG CAG AGA ATG ATC AGA TAC TCA GCT ACA CTT TTT GTG CAG
 S   N   L   R   L   Q   R   M   I   R   Y   S   A   T   L   F   V   Q 1575            1584            1593            1602            1611            1620
GAA AAG TTG CTT GGT TTG ATG TCA CTG CCA ACC AAA GAA CAG TTT GAG GAA CTG
 E   K   L   L   G   L   M   S   L   P   T   K   E   Q   F   E   E   L 1629            1638            1647            1656            1665            1674
AAA AAG AAA AGG GAA GAG ATG GAG AGG AAG AGG GCC GTG GAG AGA CAA GCT
 K   K   K   R   E   E   M   E   R   K   R   A   V   E   R   Q   A 1683            1692            1701            1710            1719            1728
GCC CTG GAG TCC CAG CGA AGG CTT GAG GAA AGG CTT GAG CAG AGT GGC CTG GCT TCT CGA
 A   L   E   S   Q   R   R   L   E   E   R   Q   S   G   L   A   S   R 1737            1746            1755            1764            1773            1782
GCC AAC GGG GAG GTG GCA TCT CTC CGC AGG GGC CCT GCC CCC TTG AGA AAG
 A   N   G   E   V   A   S   L   R   R   G   P   A   P   L   R   K
```

FIGURE 1F

FIGURE 1G

```
      1791              1800              1809              1818              1827              1836
GCT   GAG   GGC   TGG   CTC   CCA   CTG   TCA   GGA   GGT   CAG   GGG   CAG   AGT   GAG   GAC   TCA   GAC
---   ---   ---   ---   ---   ---   ---   ---   ---   ---   ---   ---   ---   ---   ---   ---   ---   ---
 A     E     G     W     L     P     L     S     G     G     Q     G     Q     S     E     D     S     D 1845              1854              1863              1872              1881              1890
CCG   CTC   CTC   CAG   CAG   ATC   CAC   AAC   ATC   ACA   TCA   TTC   ATC   AGG   CAG   GCC   AAG   GCC
---   ---   ---   ---   ---   ---   ---   ---   ---   ---   ---   ---   ---   ---   ---   ---   ---   ---
 P     L     L     Q     Q     I     H     N     I     T     S     F     I     R     Q     A     K     A 1899              1908              1917              1926              1935              1944
GCG   GGC   ATG   GAT   GAA   GTG   CGC   ACT   CTG   CAG   GAG   AAC   CTG   CGG   CAG   CTG   CAG
---   ---   ---   ---   ---   ---   ---   ---   ---   ---   ---   ---   ---   ---   ---   ---   ---
 A     G     M     D     E     V     R     T     L     Q     E     N     L     R     Q     L     Q 1953              1962              1971              1980              1989              1998
GAC   TAT   GAC   CAG   CAG   ACA   GAG   AAG   GCC   ATC   GAG   CTG   TCC   CGG   AGG   CAG
---   ---   ---   ---   ---   ---   ---   ---   ---   ---   ---   ---   ---   ---   ---   ---
 D     Y     D     Q     Q     T     E     K     A     I     E     L     S     R     R     Q 2007              2016              2025              2034              2043              2052
GAC   GAG   GAG   GAC   CAG   CTG   CAG   CGG   GAA   CAG   ACA   CAG   ATG   TTG   CGT   GAA   CGG   GAG
---   ---   ---   ---   ---   ---   ---   ---   ---   ---   ---   ---   ---   ---   ---   ---   ---   ---
 D     E     E     D     Q     L     Q     R     E     Q     T     Q     M     L     R     E     R     E 2007              2016              2025              2034              2043              2052
GCT   GAG   GAG   GAG   GAC   CTG   CAG   CGG   GAA   CAG   CTG   CAG   ATG   TTG   CGT   GAA   CGG   GAG
---   ---   ---   ---   ---   ---   ---   ---   ---   ---   ---   ---   ---   ---   ---   ---   ---   ---
 A     E     E     E     D     L     Q     R     E     Q     L     Q     M     L     R     E     R     E
```

```
      2061            2070           2079           2088           2097           2106
TTG GAA CGA GAA AGG GAG CAG TTT CGG GTG GCA TCC CTG CAC ACA CGG ACT CGG
 L   E   R   E   R   E   Q   F   R   V   A   S   L   H   T   R   T   R 2115            2124           2133           2142           2151           2160
TCC CTG GAC TTC AGA GAA ATC GGC CCT TTT CAG CTG GAG CCC AGC AGA GAG CCT
 S   L   D   F   R   E   I   G   P   F   Q   L   E   P   S   R   E   P 2169            2178           2187           2196           2205           2214
CGC ACC CAC CTT GCT TAT GCT TTG GAT CTA GGC TCT TCC CCA GTT CCA AGC AGC
 R   T   H   L   A   Y   A   L   D   L   G   S   S   P   V   P   S   S 2223            2232           2241           2250           2259           2268
ACA GCT CCC AAG ACC CCT TCA ACT CTT AGC TCA ACT CAA CCC ACC AGA GTG TGG TCT
 T   A   P   K   T   P   S   T   L   S   S   T   Q   P   T   R   V   W   S 2277            2286           2295           2304           2313           2322
GGG CCC CCA GCC GTT GGC CAG GAG CGC TTA CCC CAG AGC AGC ATG CCA CAG CAA
 G   P   P   A   V   G   Q   E   R   L   P   Q   S   S   M   P   Q   Q
```

FIGURE 1H

FIGURE 1I

```
     2331              2340              2349              2358              2367              2376
CAT GAG GGG   CCC TCC AAC   CCC TTT GAT   GAG GAA GAC   CTC TCC AGC   CCC ATG
 H   E   G     P   S   N     P   F   D     E   E   D     L   S   S     P   M 2385              2394              2403              2412              2421              2430
GAA GAG GCC   ACT ACT GGT   CCT CCT GCA   GGG GTT TCC   TTA GAC CCT   TCA GCC
 E   E   A     T   T   G     P   P   A     G   V   S     L   D   P     S   A 2439              2448              2457              2466              2475              2484
CGC ATC CTG   AAA GAG TAC   AAT CCA TTC   GAG TTC GAG   GAA GAG GAA   GCA
 R   I   L     K   E   Y     N   P   F     E   F   E     E   E   E     A 2493              2502              2511              2520              2529              2538
GTG GCA GGG   AAT CCA TTC   ATT CAG CCA   GAC AGC CCA   GCT CCT AAC   CCC TTC AGT
 V   A   G     N   P   F     I   Q   P     D   S   P     A   P   N     P   F   S 2547              2556              2565              2574              2583              2592
GAG GAA GAC   GAA CAT CCC   CAG CAG AGG   CTC TCA AGC   CCT CTG GTT   CCT GGT AAC
 E   E   D     E   H   P     Q   Q   R     L   S   S     P   L   V     P   G   N
```

```
      2601         2610         2619         2628         2637         2646
CCC TTT GAG GAA CCC ACC TGT ATC AAC CCC TTT GAG ATG GAC AGT GAC AGT GGG
 P   F   E   E   P   T   C   I   N   P   F   E   M   D   S   D   S   G 2655         2664         2673         2682         2691         2700
CCA GAG GCT GAG GAG CCC ATA GAG GAA GAG CTC CTG CAG CAG ATC GAT AAC
 P   E   A   E   E   P   I   E   E   E   L   L   Q   Q   I   D   N 2709         2718         2727         2736         2745         2754
ATC AAG GCA TAC ATC TTT GAT GCC AAG CAG TGC GGC CGC CTG GAT GAG GTA GAG
 I   K   A   Y   I   F   D   A   K   Q   C   G   R   L   D   E   V   E 2763         2772         2781         2790         2799         2808
GTG CTG ACA GAG AAT CTG CGG GAG CTG AAG CAC ACC CTG GCC AAG CAG AAG GGG
 V   L   T   E   N   L   R   E   L   K   H   T   L   A   K   Q   K   G 2817         2826         2835         2844         2853         2862
GGC ACT GAC TGA CCA GCA GTG GAG AGG GCA CCT TTG GGC CCA GGG GTC TGG CAG
 G   T   D   *
```

FIGURE 1J

```
      2871         2880         2889         2898         2907         2916
GAG CCA GTG GAG CAG CAG AGA GGG CAG GCA GGA TGG ATG GGG AAG GTG GCA GGG
      2925         2934         2943         2952         2961         2970
TGA GAA CTC AGA TGC ACA CAG GTG AGG GGC AGG AAT CTG TTT TGT GTT GCG
      2979         2988         2997         3006         3015         3024
CAC TTT GAG GTA TTT CCA CTA CAG TTG AAT AAT AAA ATA GAA ACT AGA ACA GGG
      3033         3042         3051         3060         3069         3078
AGA ATC AGC ATT CAG CTG CTG CTT TTC CTG TTT ATT ATT ACT ATC TTT TGT AAT
      3087         3096         3105         3114         3123         3132
CGG AGG TTT ACC CCT TTT GAA GGG ACT TTA CAT TTT TAC TAC CGA GAT ATA ACT
      3141         3150         3159         3168         3177         3186
AAA TGC AGC TCT GTT GGG CCC AGG GCA GAA ATG GCT GCT GTG TAC CTC TTG GGT
      3195         3204         3213         3222         3231         3240
CCA TTT GCT ACT GCC TAG TCT TGG TTC CTT ATG CAG TAT TAT AGG GCA GCC TTT
      3249         3258         3267         3276         3285         3294
TTA GAG CCC TTC CTT TAG CCA AGA CAG AGA AGA TAG ATT CCA CTG AGC TCT ATT
```

FIGURE 1K

```
     3303         3312         3321         3330         3339         3348
CTG CTC TGA CAG AAG TCC ATC CCT AGT AGG CTG TGA GTT CCA TTT CAC CTG GGG
     3357         3366         3375         3384         3393         3402
CCG CCT CTC CCC TGC TCT GCA CTT CCT GTC TGT ACA ATA GAA GGG GGA GGT GCT
     3411         3420         3429         3438         3447         3456
GCT ATG AAG GGG AGA GTT TAG ACC CAG GAG AGC CAG GCA CCT CTC TTT AAG GTG
     3465         3474         3483         3492         3501         3510
GGG TGA TGG GAA TAT TTC ACC AGG GTC TAT TTT CTC AGT TTA AGT TCT TTT TTG
     3519         3528         3537         3546         3555         3564
TCT CTT TCA GGA AGT TAA GCT CCC AGT GCA GGG TAT CAA TGT GAA TCT GGT CCT
     3573         3582         3591         3600         3609         3618
GAG CTT TTT AGA AAA TAA GAG TGG TGG CCG GGC GCG CTG GCT CAC GCC TGT AAT
     3627         3636         3645         3654         3663         3672
CGC AAC ACT TTG GGA GGC CGA GGC AGG CAG ATC ACA AGG TCA GGA GAT CGA GAC
     3681         3690         3699         3708         3717         3726
CAC CCT GGC TAA CAC AGT GAA ATC CCG TCT CTA AAA ATA CAA AAA ATT AGC
```

FIGURE 1L

```
                3735            3744            3753            3762            3771            3780
CAG GCG TGG TGG TGG CCT GTG GTC CCG GCT ACT TTG GAG GCT GAG GCA GGA
        3789            3798            3807            3816            3825            3834
GAA TGC TGT GAA CCC GGG AGG CAG AGC TTG CAG TGG GCC GAG ATC GCA CCA CTG
        3843            3852            3861            3870            3879            3888
CAC TCC AGC CTG GGC AGT GAG AGT GAG ACT CCG TCT CAA AAA AAA ATA AGA GTG
        3897            3906            3915            3924            3933            3942
GTT AAC TTT TTG GTT GAT ATT AGT ATT TGT GAG AAG AGT TTC CCC ACC CTT
        3951            3960            3969            3978            3987            3996
CTT CTG ATA GAA CAA TTG TCT GTC ACT GGA GAA ATC TCC CTC CAG AGC TTT GGC
        4005            4014            4023            4032            4041            4050
AAA GTT ACT CTG ATC TGG GTC TGT TTA AAA GGC CGG GTC TCT AAT TTA GGA ATC
        4059            4068            4077            4086            4095            4104
GGT GAT TTG GAA GCT TTT GCA GAA CAT CAC CAG AAG GGA AGC TTC CCA GAG
        4113            4122            4131            4140            4149            4158
TCA GAA GCT AAA TTA AAA TAA TTT CCA AGG CTA TTT GAT CAG CCT TCT TCC TTT
```

FIGURE 1M

```
4167              4176              4185              4194              4203              4212
TTG GTT CAT     TGT GTC CTG     ACT TGG GGC     ACT GAT GAG     ATT TTT TAT     TTT TTT TGA 4221              4230              4239              4248              4257              4266
GAC GGA GTT     TCA CTT TGT     TGC CCA GGC     TGG AGT GTA     GTG GCA TGA     TCT CGG CTC 4275              4284              4293              4302              4311              4320
ACT GCA ACC     TCC ACC CTG     GTT CAA GTG     ATA TTT GTG     CCT CAG CCC     CCT GAA 4329              4338              4347              4356              4365              4374
TAG CTG GGA     TTA CAG GCG     TGG GCC ACC     ACG CCT GGT     TAA TCT CTG     TAT TTT TGG 4383              4392              4401              4410              4419              4428
TAG AGG TAG     AGT TTC ACC     ATT TTG GCC     AGG CTG GTT     TCG AAC TCC     TGG CCT CAA 4437              4446              4455              4464              4473              4482
GTG ATC TGC     CAC CTT GGC     CTC CCA AAG     TGC TGG GAA     TAC AGG CGT     GAG CCA CTG 4491              4500              4509              4518              4527              4536
TGC CCG CCC     TGA TGA GAT     ATT TTA CCA     ATG TTA GTA     TTG AGA AAC     TGA AAT 4545              4554              4563              4572              4581              4590
GTT TGA AGA     AGC ACA ACC     CAG GAT CGT     GCT GGT AGC     ACC ACA GTA     CTT AAA CTG
```

FIGURE 1N

```
         4599              4608              4617              4626              4635              4644
TTG GTC AAT TAA GGC CAG AAA GGG AAA TTG TTA ATT TAG CTC TGG TGC TTT GGT
         4653              4662              4671              4680              4689              4698
TTA CAG GAA CAT AAC TCT TAA CTG ACA TCT GAC ATC ATG ATA GCC ATA TGT GCT
         4707              4716              4725              4734              4743              4752
CAG CTC TGG GTA GAG TTT CTG CAG TTA CTC ATC TGA ACT AAT GAA CAA TAA CTG
         4761              4770              4779              4788              4797              4806
ACC ACT AGT CAC TTT ATG CCG TGT AAC TAG CTC TAG GCC ATA CTT TCA CTG GTT
         4815              4824              4833              4842              4851              4860
ACT GGT GTG AAA GCT GAA ATT CAT TTT GTT ACA TTC TGG TGA AGA CCC CTC TTG
         4869              4878              4887              4896              4905              4914
ATA ATG GGA ATG TTT TAA CTC TCT TGA TGA AAA AAT AAT CTG TAT TTG TGT TGA
         4923              4932              4941              4950              4959              4968
TGT TCA CAT TTC TGT AGC ACA TTT CTT ATC CTT TTG GTT GAA TGA AAA GAT CTT
         4977              4986              4995              5004              5013              5022
GTA TAG GGG TGT GGA GAT GGG GAG TGG GTA GAA GTG TGT GAA GGA CGC TTT GCA
```

FIGURE 10

```
        5031              5040              5049          5058              5067              5076
TTT GGG ATC TGT TCA CAA ACA GCC ATA TGA GTG TGT TAA TGA ATG TCA GCC AGT 5085              5094              5103         5112              5121              5130
TAC CAA CCC TGC TGG TTG TTA TGG GTT GTT TTG AGA AGT TGG CAA CCA GGC ATC 5139              5148              5157         5166              5175              5184
TAA GAT GTT GCC TGG TAC AGG CCT CTT TTC TTC CCT GAG GCC CAT GAC ATT TCT 5193              5202              5211         5220              5229              5238
CTG TTA CTC TAG AGG GTT TCT CAG ATG GCC AGT AGG CTC CTC CCT GCT TAG GGT 5247              5256              5265         5274              5283              5292
CTC ATT TCT CTG AAA AGA GGA TGA ACT GAA AAG CAG GTA GTT CCA GAA GCT AAT 5301              5310              5319         5328              5337              5346
TGC TGC TTT CCA TCA TAA TTA TTT TTC TTG TGA GAA CAT TTC TCT TTT AAT TAG 5355              5364              5373         5382              5391              5400
CTA GTG ATT TTG ATT AAG ACT AAT TCA CTA AAC ATA CCC TTC CCT CAA ATC ACC 5409              5418              5427         5436              5445              5454
TCA GGT AGC AAT CTG TAA GTA ACT AAA AGC ATT GAA AAA CAC ACA AGA AAC ATT
```

FIGURE 1P

```
        5463           5472           5481           5490           5499           5508
TTT AAA AAC TAT TTT TAA AGG CCT GGC CGG GTG CAG TGG CTC ACT CCT GTA ATC
        5517           5526           5535           5544           5553           5562
CCA GCA CTT TGG GAG GCC GAG ACG GGT GGA TCA CCT GAG GTC AGG AAT TTG AGA
        5571           5580           5589           5598           5607           5616
CTA GCA TGG CCA ACA TGG TGA AAC CCC GTG TCT ACT AAA AAT ACA AAA ATT AGC
        5625           5634           5643           5652           5661           5670
TGG GCG TGG TGG CAG ACG CCT GTA ATC CCA GCT ACT CAG GGA GGC TGA GGC ACG
        5679           5688           5697           5706           5715           5724
AGA ATC GCT TGA ACC TGG GAG GCG GAG GTT GCA GTG AGC CAA GAT TGC GCC ACT
        5733           5742           5751           5760           5769           5778
GCA CTC CAA CCT GGG TGA CAA GAG CAA GAC TCC GTC TCA CAA AAA ACA AAC AAA
        5787           5796           5805           5814           5823           5832
ACT GAC TGA TTG AAT ATA CTA AAC CAA ACT AAA ATC ATA TTC TTT TGA TTA AGT
        5841           5850           5859           5868           5877           5886
TTA TCC ATG GCT GTA TTC TTC TAT GAA TTC TTC CAT TTA ATT CTT CCA CGA TTA
```

FIGURE 1Q

```
      5895        5904        5913        5922        5931        5940
TCT TCT CCT GTA AAT ACA TCA CAG GAG TTA GAA TTC TCT ACC CAT CAG CTG TAC
      5949        5958        5967        5976        5985        5994
CAT GTC GCA GAA TTC ATG CAG GCA CAA AGT TGG AGT TAC AGA GAT GGG TTG ACA
      6003        6012        6021        6030        6039        6048
GCA GGC AAA CTT GGC CTA TGT ATT ATA ACC ACA ACT TCA AGT TCT TAC CTC ATG
      6057        6066        6075        6084        6093        6102
TGA ATA TTC ACC CTT TCT TTA GTC TTC CAA GGC AAA CAG CCC CGT CTC ATC ACC
      6111        6120        6129        6138        6147        6156
AGA TGA GCA AGG TCT TGA TAT GGC ATA GCA GAT CTC CCT AGA CAC AGA TCA TGA
      6165        6174        6183        6192        6201        6210
GAA AAG ATG GAA GAG ACT TAG GGA TTC AGG CAT CAG ATG AAG TTG GCT TTT CCC
      6219        6228        6237        6246        6255        6264
TTT TAT GCC TTG TTT GTA TTT ACC CTG TCT AAT ACA CTA AGG ATA CTT ACT CAT
      6273        6282        6291        6300        6309        6318
TGT ACT TGC AGC TCA ATA TGT CTT TGC TGT TCA GAT ACT AAA ATG TAC CTC TGA
```

FIGURE 1R

```
      6327            6336            6345            6354            6363            6372
GTC ATT GTG AGC TGT GTG GTA GGT TGG ACA TTG GCA TAG TTG GTG ATG GGA CTC
      6381            6390            6399            6408            6417            6426
AAA ATG AAA AGG TGG TCT CTT TAC CAG GTC ACA GAC TGT AGC AGA TTG TGC TTG
      6435            6444            6453            6462            6471            6480
TTA TCT GAC AAT GAC TGT CAC TTT GAG GGT CGT TGA TTT GCA TGC ACT ACT CTG
      6489            6498            6507            6516            6525            6534
GGG CCT TGT ATT GGA GCC TTT TTT AAA AAT AAA ATC TGA GAT AGA GGT TGG
      6543            6552            6561            6570            6579            6588
GGG TGT GTG TGT CTG TGT GCA CAT GTG TTA CAA GTG AGA ATC ATC AGA TGA CAT
      6597            6606            6615            6624            6633            6642
CCC TTC TCC TTT CTT GAT GAC AAC CAT CTG AGT ATC AGA ATA GTT CCA GCA CCT
      6651            6660            6669            6678            6687            6696
GTG TTT GTC TGG TTA AGG CCT CTG GAA AAA ATG AAG GTC ACT GGG TTC TGA
      6705            6714            6723            6732            6741            6750
ACA GGG GAT AGA TAC GGG TTC CAG TTC TGC CCT TAT TCC CAG TTA TTC CTG CAG
```

FIGURE 1S

```
      6759           6768           6777           6786           6795           6804
TGC TGG TTA AAT GAA CAG TTT TAC AGA AGT ATA GTG CAG ATC CCT TAA TGA TCC
      6813           6822           6831           6840           6849           6858
TAT CAT CCC AGT TTC ACA CTG GAA GAA ACT GAG GCT CAG AGA TTG AGG AAC CTT
      6867           6876           6885           6894           6903           6912
GTG ACT GCC ATC TGT GCC AGT CAC CAC CTC TGC ATG ACC ACA TTT CCC TCC ATT
      6921           6930           6939           6948           6957           6966
AGC ACT ACC AGC ATG CCT GTG AGG TAG TTA CTC AGC TGT TCA TCT GAC CCC AGA
      6975           6984           6993           7002           7011           7020
CGT AGA AAA GTT AAG AGA GAT TAG CCT GGC TTA GGC CAC ACA GCC AGT CAG TGG
      7029           7038           7047           7056           7065           7074
TGG AAT GAG GGT TTA AAT CCA GAT CTG CCT GAC TTA ATT TGC CCT CAG TAA TAA
      7083           7092           7101           7110           7119           7128
GTA GCT GGG TCA GGT AGT GGT GTG GTG GGT GCT CAA CCA TTG TGT CAA
      7137           7146           7155           7164           7173           7182
GCT CAA AGA GGG CAG AAA AGG GCA ATG GGG AAT GAG GTT GGG TGC TGA GCT
```

FIGURE 1T

```
      7191              7200              7209        7218              7227        7236
GGT TTC CGA TAG TGA CTG CCT GAG TCT GTG AAA CTG AGA CCT CCT TAG GGC CTT 7245              7254              7263        7272              7281        7290
AAG AAT ATA TAG ATT CTT AAA CCA GGA GAG TAT AAT ATC TAG TGC TCA CTG TAG 7299              7308              7317        7326              7335        7344
GCT AGA CTG AGT GCT AAG TAT TAC GCA TGG CTT ACC TCA GTC TTC CCA ACA ACC 7353              7362              7371        7380              7389        7398
CAT TTA CAC ATG CAG AAA TGA GTG AGT GGT GAA GTT AAG CTT GCT TAG GGT TGC 7407              7416              7425        7434              7443        7452
ACT GCT GGG TTT CCA GCC TAG GTC TGT CTG ACT GCA AAA CCC AAG CTG CCC TAG 7461              7470              7479        7488              7497        7506
ATT GTG TTG TAT GTG GAC ACC CAT GTT TCT AAT GTG GAA TGG GGT GTT TCA TCC 7515              7524              7533        7542              7551        7560
CTA GCA AGT GCC TCC TGT GGA CTT TTA AGA TGA AAA ACT TCT GCC TAA CTC TTC 7569              7578              7587        7596              7605        7614
AGG AAG CCT AGC GTA GTT GTA AAA ATA CTT CAG AAA GCA CTT CTG GTT TTA GCT
```

FIGURE 1U

```
         7623           7632           7641           7650           7659           7668
CAG ACA CGT AGA GTT TGA AAG TTA TCC TAT CCT TAC CAC AAG AAA AAG CTG GGC
         7677           7686           7695           7704           7713           7722
AAA CTC AAA AGC ATT GGC CTT TCT TGG TCC CAT TAG AGA GCT GAG TGT GCA GGT
         7731           7740           7749           7758           7767           7776
CAA ACT GCC ATC CCA AAA TCT AGA GAG AGG TGA GTC CAG AGA GTG AGC AAG ATC
         7785           7794           7803           7812           7821           7830
TAA TTG CCT GGA GCA GAA GCC ACG GGA GCC ATA GCT AGT AGG AAA ACT TAA ATG
         7839           7848           7857           7866           7875           7884
GTA ATT TTG ATG AAC TGC TGG AGG TTG AGT GTG GAC TAG CAT GGG AGG GAG CAA
         7893           7902           7911           7920           7929           7938
CTC CCC CTC ACC CCC AAC GCT TTC CTG GGT TTT ACC CTA CTT GGT TCT ATT GGT
         7947           7956           7965           7974           7983           7992
GAA GAG CTG AGG AAG ACC CTC TGG TGA CTC TGG CAG GGG AAA GGG AGA ATC ATC
         8001           8010           8019
TTT GTA ATC AGA GCC TTC TCC ATA ATA AA 3'
```

FIGURE 1V

COLON CANCER MARKER

FIELD OF THE INVENTION

This invention relates to a mammalian cDNA which encodes a colon cancer marker and to the use of the cDNA and the encoded protein in the diagnosis and treatment of colon disorders, particularly colon cancer and polyps.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Colorectal cancer is the fourth most common cancer and the second most common cause of cancer death in the United States with approximately 130,000 new cases and 55,000 deaths per year. Colon and rectal cancers share many environmental risk factors and both are found in individuals with specific genetic syndromes (Potter (1999) J Natl Cancer Institute 91:916–932). Colon cancer is the only cancer that occurs with approximately equal frequency in men and women, and the five-year survival rate following diagnosis of colon cancer is around 55% in the United States (Ries et al. (1990) National Institutes of Health, DHHS Publ. No. (NI)90-2789).

Colon cancer is causally related to both genes and the environment. Several molecular pathways have been linked to the development of colon cancer, and the expression of key genes in any of these pathways may be affected by inherited or acquired mutation or by hypermethylation. There is a particular need to identify genes for which changes in expression may provide an early indicator of colon cancer or a predisposition for the development of colon cancer.

For example, it is well known that abnormal patterns of DNA methylation occur consistently in human tumors and include, simultaneously, widespread genomic hypomethylation and localized areas of increased methylation. In colon cancer in particular, it has been found that these changes occur early in tumor progression such as in premalignant polyps that precede colon cancer. Indeed, DNA methyltransferase, the enzyme that performs DNA methylation, is significantly increased in histologically normal mucosa from patients with colon cancer or in the benign polyps that precede cancer. This increase continues during the progression of colonic neoplasms (El-Deiry et al. (1991) Proc Natl Acad Sci USA 88:3470–3474). Increased DNA methylation occurs in G+C rich areas of genomic DNA termed "CpG islands" that are important for maintenance of an "open" transcriptional conformation around genes, and hypermethylation of these regions results in a "closed" conformation that silences gene transcription. It has been suggested that the silencing or downregulation of differentiation genes by such abnormal methylation of CpG islands may prevent differentiation in immortalized cells (Antequera et al. (1990) Cell 62:503–514).

Familial adenomatous polyposis (FAP) is a rare autosomal dominant syndrome that precedes colon cancer and is caused by an inherited mutation in the adenomatous polyposis coli (APC) gene. FAP is characterized by the early development of multiple colorectal adenomas that progress to cancer at a mean age of 44 years. The APC gene is a part of the APC-β-catenin-Tcf (T-cell factor) pathway. Impairment of this pathway results in the loss of orderly replication, adhesion, and migration of colonic epithelial cells that results in the growth of polyps. A series of other genetic changes follow activation of the APC-β-catenin-Tcf pathway and accompanies the transition from normal colonic mucosa to metastatic carcinoma. These changes include mutation of the K-Ras proto-oncogene, changes in methylation patterns, and mutation or loss of the tumor suppressor genes p53 and Smad4/DPC4. While the inheritance of a mutated APC gene is a rare event, the loss or mutation of APC and the consequent effects on the APC-β-catenin-Tcf pathway is believed to be central to the majority of colon cancers in the general population.

Hereditary nonpolyposis colorectal cancer (HNPCC) is another inherited autosomal dominant syndrome with a less well defined phenotype than FAP. HNPCC, which accounts for about 2% of colorectal cancer cases, is distinguished by the tendency to early onset of cancer and the development of other cancers, particularly those involving the endometrium, urinary tract, stomach, and biliary system. HNPCC results from the mutation of one or more genes in the DNA mis-match repair (MMR) pathway. Mutations in two human MMR genes, MSH2 and MLH1, are found in a large majority of HNPCC families identified to date. The DNA MMR pathway identifies and repairs errors that result from the activity of DNA polymerase during replication. Furthermore, loss of MMR activity contributes to cancer progression through accumulation of other gene mutations and deletions, such as loss of the BAX gene which controls apoptosis, and the TGFβ receptor II gene which controls cell growth. Because of the potential for irreparable damage to DNA in an individual with a DNA MMR defect, progression to carcinoma is more rapid than usual.

Although ulcerative colitis is a minor contributor to colon cancer, affected individuals have about a 20-fold increase in risk for developing cancer. Progression is associated with mutations in the p53 gene which may occur early, appearing even in histologically normal tissue. The progression of the disease from ulcerative colitis to dysplasia/carcinoma without an intermediate polyp state suggests a high degree of mutagenic activity resulting from the exposure of proliferating cells in the colonic mucosa to the colonic contents.

Almost all colon cancers arise from cells in which the estrogen receptor (ER) gene has been silenced. The silencing of ER gene transcription is age related and linked to hypermethylation of the ER gene (Issa et al. (1994) Nature Genetics 7:536–540). Introduction and expression of an exogenous ER coding sequence into cultured colon carcinoma cells results in marked suppression of growth. Inhibition of cancer cell invasion depends on the function of the hormone binding domain and the N-terminal zinc finger region of the ER (Platet et al. (2000) Mol Endocrinol 14:999–1009). Activation of the ER by hormone binding induces transcription of specific target genes and may be linked to the reduction in cancer invasiveness. In the absence of hormone, protein-protein interactions with the zinc finger region may also contribute to the inhibition of cancer cell migration. The connection between loss of the ER protein in colonic epithelial cells and the consequent development of cancer has not been established.

The FYVE-finger proteins play roles in cellular processes such as receptor signaling, vesicular trafficking, and actinregulated membrane rearrangements (Stenmark and Aasland (1999) J Cell Science 112:4175–4183). The FYVE domain is a type of zinc finger that typically contains eight conserved cysteines which bind two $Zn^{2+}$ cations, has conserved glycine and arginine residues, and a basic motif with the consensus sequence R(R/K)HHCR. The FYVE domain binds to phosphoinositides found in specific membranes. The presence of other domains in FYVE-finger proteins may mediate protein—protein interactions with other molecules at the membrane and may be involved in the recruitment of signaling molecules such as small GTPases to membranes at particular cellular locations. In mice with a null muation in the FYVE finger protein Hrs, embryos showed defects in ventral folding morphogenesis and died in utero (Komada and Soriano (1999) Genes Dev 13:1475–1485). The embryos developed with their ventral region outside of the yolk sac, had two independent bilateral heart tubes, and no foregut. Mutations in genes that control cellular differentiation and proliferation in the intestine may be linked with colon disease (Dove et al. (1998) Phil Trans R Soc Lond B 353:915–923).

Clearly there are a number of genetic alterations associated with colon cancer and with the development and progression of the disease. Particularly, downregulation of expression or deletion of genes potentially provide early indicators of cancer development, and may also be used to monitor disease progression or provide possible therapeutic targets. The specific genes affected in a given case of colon cancer depend on the molecular progression of the disease. Identification of additional genes associated with colon cancer and the precancerous state would provide more reliable diagnostic patterns associated with the development and progression of the disease.

The discovery of a mammalian cDNA encoding a colon cancer marker satisfies a need in the art by providing compositions which are useful in the diagnosis and treatment of colon disorders, particularly colon cancer and polyps.

SUMMARY OF THE INVENTION

The invention is based on the discovery of a mammalian cDNA which encodes a colon cancer marker (CCM), which is useful in the diagnosis and treatment of colon disorders, particularly colon cancer and polyps.

The invention provides an isolated mammalian cDNA or a fragment thereof encoding a mammalian protein or a portion thereof selected from the group consisting of an amino acid sequence of SEQ ID NO:1, a variant having at least 85% identity to the amino acid sequence of SEQ ID NO:1, an antigenic epitope of SEQ ID NO:1, and a biologically active portion of SEQ ID NO:1. The invention also provides an isolated mammalian cDNA or the complement thereof selected from the group consisting of a nucleic acid sequence of SEQ ID NO:2, a variant having at least 87% identity to the nucleic acid sequence of SEQ ID NO:2, a fragment of SEQ ID NOs:3–22, an oligonucleotide of SEQ ID NOs:2–34. The invention additionally provides a composition, a substrate, and a probe comprising the cDNA, or the complement of the cDNA, encoding CCM. The invention further provides a vector containing the cDNA, a host cell containing the vector and a method for using the cDNA to make CCM. The invention still further provides a transgenic cell line or organism comprising the vector containing the cDNA encoding CCM. The invention additionally provides a mammalian fragment or the complement thereof selected from the group consisting of SEQ ID NOs:23–34. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose colon disorders, particularly colon cancer and polyps. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified mammalian protein or a portion thereof selected from the group consisting of an amino acid sequence of SEQ ID NO:1, a variant having 85% identity to the amino acid sequence of SEQ ID NO:1, an antigenic epitope of SEQ ID NO:1, and a biologically active portion of SEQ ID NO:1. The invention also provides a composition comprising the purified protein or a portion thereof in conjunction with a pharmaceutical carrier. The invention further provides a method of using the CCM to treat a subject with colon disorders, particularly colon cancer and polyps comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with colon disorders, particularly colon cancer and polyps.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of colon disorders, particularly colon cancer and polyps.

The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to a protein which is expressed in colon disorders, particularly colon cancer and polyps. The invention also provides a method of using an antibody to diagnose colon disorders, particularly colon cancer and polyps comprising combining the antibody comparing the quantity of bound antibody to known standards, thereby establishing the presence of colon disorders, particularly colon cancer and polyps. The invention further provides a method of using an antibody to treat colon disorders, particularly colon cancer and polyps comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:2–34, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A, 1B, 1C, 1D, 1E, 1F, 1G, 1H, 1I, 1J, 1K, 1L, 1M, 1N, 1O, 1P, 1Q, 1R, 1S, 1T, 1U and 1V show the mammalian CCM (SEQ ID NO:1) encoded by the cDNA (SEQ ID NO:2). The translation was produced using MACDNASIS PRO software (Hitachi Software Engineering, South San Francisco Calif.).

Table 1 shows the differential expression of CCM in colon cancer and colon polyps relative to normal colon tissue as determined by microarray analysis. Column 1 lists the mean differential expression (DE) values presented as log2 DE (diseased tissue/microscopically normal tissue) for tissue samples from patients with colon cancer and colon polyps. Column 2 lists the percentage covariance (CV%) in differential expression values. Column 3 lists the tissue and patient donor (Dn) for microscopically normal samples labeled with fluorescent green dye Cy3. Column 4 lists the tissue and patient donor (Dn) for diseased samples labeled with fluorescent red dye Cy5.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"CCM" refers to a substantially purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a cDNA of the Sequence Listing refers to a nucleic acid molecule which is completely complementary over its full length and which will hybridize to the cDNA or an mRNA under conditions of high stringency.

"cDNA" refers to an isolated polynucleotide, nucleic acid molecule, or any fragment or complement thereof. It may have originated recombinantly or synthetically, be double-stranded or single-stranded, represent coding and/or non-coding 5' and 3' sequence.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provides identity within the conserved region.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the cDNAs and CCM are differentially expressed such as colon disorders, particularly colon cancer and polyps.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of a mammalian cDNA which encodes a colon cancer marker and on the use of the cDNA, or fragments thereof, and protein, or portions thereof, directly or as compositions in the characterization, diagnosis, and treatment of colon disorders.

Nucleic acids encoding CCM of the present invention were first identified in Incyte Clone 5098390 from the mammary epithelial cell cDNA library (EPIMNON05) using a computer search for amino acid sequence alignments. A consensus sequence, SEQ ID NO:2, was derived from the following overlapping and/or extended nucleic acid sequences (SEQ ID NOs:3–22): Incyte Clones 5098390F6 (EPIMNON05), 8022266J1, 7394066H1, 6309461H1 (NERDTDN03), 7436032H1, 7676140H2, 6923049H1 (PLACFER06), 8216794J1, 6995895H1 (BRAQTDR02), 6889439H1 (BRAITDR03), 70405975D1 (SG0000195), 8117068H1, 747646H1 (BRAITUT01), 7984383H1, 8073132J1, 6744627H1 (BRAFNOT02), 6749637H1 (BRAXNOT03), 5073165F8 (COLCTUT03), 6441214H1 (BRAENOT02), 2436362H1 (BRAVUNT02), and GenBank EST g921283 (SEQ ID NO:35), and genomic sequence GNFL.g8572864_000002_002.edit (SEQ ID NO:36). Table 1 shows the differential expression of CCM in colon cancer and colon polyps relative to normal colon tissue as determined by microarray analysis. CCM shows reduced expression in tissues from patients with colon cancer relative to microscopically normal tissue from the same donors (Dn3753, Dn3649, and Dn3647). CCM shows reduced expression in tissue from a patient with colon adenoma relative to microscopically normal tissue from the same donor (Dn3583). CCM also shows reduced expression in tissue from a patient with colon polyps relative to microscopically normal tissue from the same donor (Dn3753). Therefore, the cDNA is useful in diagnostic assays for colon disorders, particularly colon cancer and polyps. A fragment thereof the cDNA from about nucleotide 1 to about nucleotide 50 is also useful in diagnostic assays.

In one embodiment, the invention encompasses a polypeptide comprising the amino acid sequence of SEQ ID NO:1. CCM is 784 amino acids in length and has one potential N-glycosylation site at N465; one potential cyclic AMP- or cyclic GMP-dependent protein kinase phosphorylation site at S230; ten potential casein kinase II phosphorylation sites at S3, S31, S38, T132, T137, S239, T484, S635, S691, and S726; and nine potential protein kinase C phosphorylation sites at S141, S171, S226, S333, S407, S429, T501, S508, and S654. MOTIFS analysis indicates that the region of CCM from C16 through H37 is similar to a C2H2 type zinc finger motif. BLOCKS analysis indicates that the region of CCM from C182 through M191 is similar to a C3HC4 zinc finger (RING finger) motif. Pfam analysis indicates that the region of CCM from V152 through K261 is similar to a FYVE-finger domain (E-value=3.8 $e^{-15}$). In particular, CCM has the eight conserved cysteine residues at C163, C166, C179, C182, C187, C190, C252, and C255; the RRHHCR consensus sequence at residues R175 through R179; and the conserved glycine at G183 typical of FYVE-finger proteins. Useful antigenic epitopes extend from N156 to M186, N488 to L525, and A680 to A730, and biologically active portions of CCM extend from C16 through H37 and from V152 through K261. An antibody which specifically binds CCM is useful in an assay to diagnose colon disorders, particularly colon cancer and polyps.

The invention also encompasses CCM variants. A preferred CCM variant is one which has at least about 80%, or at least about 90%, or even at least about 95% amino acid sequence identity to the CCM amino acid sequence, and which contains at least one functional or structural characteristic of CCM.

Mammalian variants of the cDNA encoding CCM were identified using BLAST2 with default parameters and the ZOOSEQ databases (Incyte Genomics). These preferred variants have from about 87% to about 95% identity to human CCM as shown in the table below. The first column shows the SEQ ID for the human cDNA (SEQ $ID_H$); the second column, the SEQ ID for the variant cDNAs (SEQ $ID_{var}$); the third column, the clone number for the variant cDNAs ($Clone_{var}$); the fourth column, the library name; the fifth column, the alignment of the variant cDNA to the human cDNA (includes the alignment of different regions of the variant cDNA with different regions of the human cDNA in some cases); and the sixth column, the percent identity to the human cDNA.

cDNA encoding CCM, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring CCM, and all such variations are to be considered as being specifically disclosed.

The cDNA and fragments thereof (SEQ ID NOs:2–34) may be used in hybridization, amplification, and screening technologies to identify and distinguish among SEQ ID NO:2 and related molecules in a sample. The mammalian cDNAs may be used to produce transgenic cell lines or organisms which are model systems for human colon disorders, particularly colon cancer and polyps and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention
cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (P Green, University of Washington, Seattle Wash.), and AUTOASSEMBLER application (Applied Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE,

| SEQ $ID_H$ | SEQ $ID_{var}$ | $Clone_{Var}$ | Library Name | $Nt_H$ Alignment | Identity |
|---|---|---|---|---|---|
| 2 | 23 | 702073518T2 | RAKITXT09 | 949–1543 | 93% |
| 2 | 24 | 702549617T1 | RACONON05 | 994–1544 | 92% |
| 2 | 25 | 702448734T1 | RASPNON05 | 1093–1544 | 93% |
| 2 | 26 | 702081830H1 | RABRTXT01 | 958–1376 | 94% |
| 2 | 27 | 702053775T1 | RAKITXT08 | 1151–1442 | 91% |
| 2 | 28 | 700883909H1 | RAVANOT01 | 721–975 | 90% |
| 2 | 29 | 700883983H1 | RAVANOT01 | 721–970 | 90% |
| 2 | 30 | 701092129H1 | RALUNOT02 | 1765–1967 | 88% |
| 2 | 31 | 702137890H2 | RABRFET07 | 397–613 | 87% |
| 2 | 32 | 701741076T1 | MNBCNON01 | 6021–6451 | 95% |
| 2 | 33 | 702769948H2 | CNLINOT01 | 1377–1833 | 88% |
| 2 | 34 | 702245053H1 | CNLUNOT01 | 3494–3542 | 93% |

These cDNAs are particularly useful for producing transgenic cell lines or organisms which model human disorders and upon which potential therapeutic treatments for such disorders may be tested.

It will be appreciated by those skilled in the art that as a result of the degeneracy of the genetic code, a multitude of Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (Applied Biosystems), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (Applied Biosystems), nested primers, and commercially available cDNA or genomic DNA libraries may be used to extend the nucleic acid sequence. For all PCR-based methods, primers may be designed using commercially available software, such as OLIGO primer analysis software (Molecular Biology Insights, Cascade Colo.) to be about 22 to 30 nucleotides in length, to have a GC content of about 50% or more, and to anneal to a target molecule at temperatures from about 55C to about 68C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the CCM, allelic variants, or related molecules. The probe may be DNA or RNA, may be single stranded and should have at least 50% sequence identity to any of the nucleic acid sequences, SEQ ID NOs:2–34. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60C, which permits the formation of a hybridization complex between nucleic acid sequences that contain some mismatches. Subsequent washes are performed at higher stringency with buffers such as 0.2×SSC with 0.1% SDS at either 45C (medium stringency) or 68C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or TRITON X-100 (Sigma-Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application W095/35505; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, or 3) an artificial chromosome construction such as human artificial chromosome (HAC), yeast artificial chromosome (YAC), bacterial artificial chromosome (BAC), bacterial P1 construction, or single chromosome cDNA libraries.

Expression

Any one of a multitude of cDNAs encoding CCM may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The *Rous sarcoma* virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired cDNA is based on DNA—DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovers of Proteins from Cell Culture

Heterologous moieties engineered into a vector for ease of purification include glutathione S-transferase (GST), 6×His, FLAG, MYC, and the like. GST and 6–His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A peptide synthesizer (Applied Biosystems). A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with CCM or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The CCM or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, cheinluminescent, or chromogenic agents, and the like, by chemical conjugation to amines, thiols and other groups present in the molecules using reagents such as BIODIPY or PITC (Molecular Probes, Eugene Oreg.).

Diagnostics

The cDNAs, fragments, oligonucleotides, complementary RNA and DNA molecules, and PNAs and may be used to detect and quantify differential gene expression, absence/presence vs. excess, expression of mRNAs or to monitor mRNA levels during therapeutic intervention. Similarly antibodies which specifically bind CCM may be used to quantitate the protein. Disorders associated with differential expression include colon disorders, particularly colon cancer and polyps. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a substantially purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; and Pound, supra).

Therapeutics

Regions of CCM (SEQ ID NO:1) show chemical and structural similarity to a FYVE-finger domain-containing protein. In addition, differential expression of CCM is highly associated with colon disorders, particularly colon cancer and polyps, as shown in Table 1. CCM clearly plays a role in colon disorders, particularly colon cancer and polyps.

In the treatment of conditions associated with increased expression of CCM, it is desirable to decrease expression or protein activity. In one embodiment, the an inhibitor, antagonist or antibody of the protein may be administered to a subject to treat a condition associated with increased expression or activity. In another embodiment, a pharmaceutical composition comprising an inhibitor, antagonist or antibody in conjunction with a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

In the treatment of conditions associated with decreased expression of CCM, it is desirable to increase expression or protein activity. In one embodiment, the protein, an agonist or enhancer may be administered to a subject to treat a condition associated with decreased expression or activity. In another embodiment, a pharmaceutical composition comprising the protein, an agonist or enhancer in conjunction with a pharmaceutical carrier may be administered to a subject to treat a condition associated with the decreased expression or activity of the endogenous protein. In an additional embodiment, a vector expressing cDNA may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding CCM. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. in one alternative, a library or plurality of cDNAs or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio-groups renders the molecule less available to endogenous endonucleases.

Screening and Purification Assays

The cDNA encoding CCM may be used to screen a library of molecules or compounds for specific binding affinity. The libraries may be aptamers, DNA molecules, RNA molecules, PNAs, peptides, proteins such as transcription factors, enhancers, repressors, and other ligands which regulate the activity, replication, transcription, or translation of the cDNA in the biological system. The assay involves combining the cDNA or a fragment thereof with the library of molecules under conditions allowing specific binding, and detecting specific binding to identify at least one molecule which specifically binds the single stranded or, if appropriate, double stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, CCM or a portion thereof may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands and the specificity of binding or formation of complexes between the expressed protein and the ligand may be measured. Specific binding between the protein and molecule may be measured. Depending on the kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein or oligopeptide or portion thereof. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. For purposes of example, preparation of the human brain posterior parietal cortex (BRAENOT02) and normalized mammary epithelial cell (EPIMNON05) libraries will be described.

I cDNA Library Construction
Brain Posterior Parietal Cortex Library

The BRAENOT02 cDNA library was constructed from brain posterior parietal cortex tissue removed from the brain of a 35-year-old Caucasian male. The frozen tissue was homogenized and lysed in TRIZOL reagent (0.8 g tissue/12 ml; Life Technologies) using a POLYTRON homogenizer (Brinkmann Instruments, Westbury N.J.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted with acid phenol-chloroform and reprecipitated with sodium acetate and ethanol. Poly(A+) RNA was isolated using the OLIGOTEX kit (Qiagen, Chatsworth Calif.).

The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were Efractionated on a SEPHAROSE CL4B column (APB), and those cDNAs exceeding 400 bp were ligated into pINCY plasmid (Incyte Genomics). The plasmid pINCY was subsequently transformed into DH5α competent cells (Life Technologies).

Normalized Mammary Epithelial Cell Library

For purposes of example, the normalization of the mammary epithelial cell library (EPIMNON05) is described.

About $3.28 \times 10^6$ independent clones of the EPIMNOT01 plasmid library in *E. coli* strain DH12S competent cells (Life Technologies) were grown in liquid culture under carbenicillin (25 mg/l) and methicillin (1 mg/ml) selection following transformation by electroporation. To reduce the number of excess cDNA copies according to their abundance levels in the library, the cDNA library was normalized in a single round according to the procedure of Soares et al. (1994, Proc Natl Acad Sci 91:9228–9232), with the following modifications. The primer to template ratio in the primer extension reaction was increased from 2:1 to 10:1. The dNTP concentration in the reaction was reduced to 150 $\mu$M for each dNTP to allow the generation of longer (400 to 1000 nt) primer extension products. The reannealing hybridization was extended from 13 to 48 hr. The single stranded DNA circles of the normalized library were purified by hydroxyapatite chromatography and converted to partially double-stranded by random priming, ligated into pINCY plasmid and electroporated into DH12S competent cells (Life Technologies).

II Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid produced by the bacteria (pSPORT 1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP kit (Edge Biosystems, Gaithersburg Md.) or the REAL PREP 96 plasmid kit (Qiagen). This kit consists of a 96-well block with reagents for 960 purifications. The recommended protocol was employed except for the following changes: 1) the bacteria were cultured in 1 ml of sterile TERRIFIC BROTH (BD Biosciences, Sparks Md.) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (Applied Biosystems) or the MEGABACE 1000 DNA sequencing system (APB). Most of the isolates were sequenced according to standard ABI protocols and kits (Applied Biosystems) with solution volumes of 0.25x–1.0x concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO primer analysis software (Molecular Biology Insights), to be about 22 to 30 nucleotides in length, to have a GC content of about 50% or more, and to anneal to the target sequence at temperatures of about 68C to about 72C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5'promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94C, three min; Step 2: 94C, 15 sec; Step 3: 60C, one min; Step 4: 68C, two min; Step 5: Steps 2, 3, and 4 repeated 20 times; Step 6: 68C, five min; Step 7: storage at 4C. In the alternative, the parameters for primer pair T7 and SK+ (Stratagene) were as follows: Step 1: 94C, three min; Step 2: 94C, 15 sec; Step 3: 57C, one min; Step 4: 68C, two min; Step 5: Steps 2, 3, and 4 repeated 20 times; Step 6: 68C, five min; Step 7: storage at 4C.

The concentration of DNA in each well was determined by dispensing 100 μl PICOGREEN quantitation reagent (0.25% reagent in 1xTE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37C in 384-well plates in LB/2x carbenicillin liquid media.

The cells were lysed, and DNA was amplified using primers, Taq DNA polymerase (APB) and Pfu DNA polymerase (Stratagene) with the following parameters: Step 1: 94C, three min; Step 2: 94C, 15 sec; Step 3: 60C, one min; Step 4: 72C, two min; Step 5: steps 2, 3, and 4 repeated 29 times; Step 6: 72C, five min; Step 7: storage at 4C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (Applied Biosystems).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorf/bl2.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: –2; Open Gap: 5 and Extension Gap: 2 penalties; Gap x drop-off: 50; Expect: 10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1\times10^{-8}$. The templates were also subjected to framreshift FASTx against GENPEPT, and homolog match was defined as having an E-value of $\leq 1\times10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding CCM that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses
Immobilization of cDNAs on a Substrate The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100C for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37C for 10 min. The labeling reaction is stopped by adding 5 µl of 0.2M EDTA, and probe is purified from unincorporated nucleotides using a PROBEQUANT G-50 microcolumn (APB). The purified probe is heated to 100C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5×buffer, 1 µl 0.1 M DTT, 3 µl Cy3 or Cy5 labeling mix, 1 µl RNase inhibitor, 1 µl reverse transcriptase, and 5 µl 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C for two hr. The reaction mixture is then incubated for 20 min at 85C, and probes are purified using two successive CHROMA SPIN+TE 30 columns (Clontech, Palo Alto Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M Na.HPO$_4$, 5 mM EDTA, pH 7) at 55C for two hr. The probe, diluted in 15 ml fresh hybridization solution, is then added to the membrane. The membrane is hybridized with the probe at 55C for 16 hr. Following hybridization, the membrane is washed for 15 min at 25C in 1 mM Tris (pH 8.0), 1% Sarkosyl, and four times for 15 min each at 25C in 1 mM Tris (pH 8.0). To detect hybridization complexes, XOMAT-AR film (Eastman Kodak, Rochester N.Y.) is exposed to the membrane overnight at −70C, developed, and examined visually.

Polymer Coated Slide-based Hybridization

Probe is heated to 65C for five min, centrifuged five min at 9400 rpm in a 5415C microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hr at 60C. The arrays are washed for 10 min at 45C in 1×SSC, 0.1% SDS, and three times for 10 min each at 45C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human, rat, monkey, and dog sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis is performed at a product score of 70. All sequences and cDNA libraries in the LIFESEQ database are categorized by system, organ/tissue and cell type. The categories include cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence is expressed are counted and shown over the total number of libraries in that category. In a non-normalized library, expression levels of two or more are significant.

IX Complementary Molecules

Molecules complementary to the cDNA, from about 5 (PNA) to about 5000 bp (complement of a cDNA insert), are used to detect or inhibit gene expression. These molecules are selected using OLIGO primer analysis software (Molecular Biology Insights). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

X Selection of Sequences, Microarray Preparation and Use

Incyte clones represent template sequences derived from the LIFESEQ GOLD assembled human sequence database (Incyte Genomics). In cases where more than one clone was available for a particular template, the 5'-most clone in the template was used on the microarray. The HUMAN GENOME GEM series 1–3 microarrays (Incyte Genomics) contain 28,626 array elements which represent 10,068 annotated clusters and 18,558 unannotated clusters. For the UNIGEM series microarrays (Incyte Genomics), Incyte clones were mapped to non-redundant Unigene clusters (Unigene database (build 46), NCBI; Shuler (1997) J Mol Med 75:694–698), and the 5' clone with the strongest BLAST alignment (at least 90% identity and 100 bp overlap) was chosen, verified, and used in the construction of the microarray. The UNIGEM V microarray (Incyte Genomics) contains 7075 array elements which represent 4610 annotated genes and 2,184 unannotated clusters.

To construct microarrays, cDNAs were amplified from bacterial cells using primers complementary to vector sequences flanking the cDNA insert. Thirty cycles of PCR increased the initial quantity of cDNAs from 1–2 ng to a final quantity of greater than 5 $\mu$g. Amplified cDNAs were then purified using SEPHACRYL400 columns (APB). Purified cDNAs were immobilized on polymer-coated glass slides. Glass microscope slides (Corning, Corning N.Y.) were cleaned by ultrasound in 0.1% SDS and acetone, with extensive distilled water washes between and after treatments. Glass slides were etched in 4% hydrofluoric acid (VWR Scientific Products, West Chester Pa.), washed thoroughly in distilled water, and coated with 0.05% aminopropyl silane (Sigma Aldrich) in 95% ethanol. Coated slides were cured in a 110° C. oven. cDNAs were applied to the coated glass substrate using a procedure described in U.S. Pat. No. 5,807,522. One microliter of the cDNA at an average concentration of 100 ng/$\mu$l was loaded into the open capillary printing element by a high-speed robotic apparatus which then deposited about 5 nl of cDNA per slide.

Microarrays were UV-crosslinked using a STRATALINKER UV-crosslinker (Stratagene), and then washed at room temperature once in 0.2% SDS and three times in distilled water. Non-specific binding sites were blocked by incubation of microarrays in 0.2% casein in phosphate buffered saline (Tropix, Bedford Mass.) for 30 minutes at 60° C. followed by washes in 0.2% SDS and distilled water as before.

XI Preparation of Samples

Tissue Samples

Matched normal colon and cancerous colon or colon polyp tissue samples were provided by the Huntsman Cancer Institute, (Salt Lake City, Utah). Donor 3311 is an 85 year-old male diagnosed with colon cancer. Donor 3753 is an individual, sex unknown, with normal colon tissue. Donor 3757 is an individual, sex unknown, diagnosed with colon cancer. Donor 3756 is an individual, sex unknown, diagnosed with colon cancer. Donor 3755 is an individual, sex unknown, diagnosed with a colon polyp. Donor 3754 is an individual, sex unknown, diagnosed with a colon polyp. Donor 3583 is a 59 year-old male diagnosed with a right colectomy, tubulovillous colon polyp, hyperplastic colon polyp, and colon adenoma. Donor 3649 is an 86 year-old individual, sex unknown, diagnosed with an invasive, well-differentiated adenocarcinoma. Donor 3647 is an 83 year-old individual, sex unknown, diagnosed with an invasive, moderately well-differentiated adenocarcinoma with metastases to the lymph nodes. Comparisons were done with matched normal and tumor or polyp tissue from the same donor. Donor 3983 is a 23 year-old individual, sex unknown, diagnosed with a polyp from adenomatous polyposis coli and with moderately differentiated adenocarcinoma that had metastasized to the lymph nodes.

XII Expression of CCM

Expression and purification of the protein are achieved using either a mammalian cell expression system or an insect cell expression system. The pUB6/V5-His vector system (Invitrogen, Carlsbad Calif.) is used to express CCM in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

Spodoptera frugiperda (Sf9) insect cells are infected with recombinant Autographica californica nuclear polyhedrosis virus (baculovirus). The polyhedrin gene is replaced with the cDNA by homologous recombination and the polyhedrin promoter drives cDNA transcription. The protein is synthesized as a fusion protein with 6xhis which enables purification as described above. Purified protein is used in the following activity and to make antibodies.

XIII Production of Antibodies

CCM is purified using polyacrylamide gel electrophoresis and used to immunize mice or rabbits. Antibodies are produced using the protocols below. Alternatively, the amino acid sequence of CCM is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XIV Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XV Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XVI Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30C until the colonies have grown up and are counted. The colonies are pooled in a minimal volume of 1xTE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

XVII CCM Assay

The localization of CCM in the intestine is detected by fluorescence microscopy as described by Boll et al. (1993; J Biol Chem 268:12901–12911). Sections of intestinal tissue are fixed with 2.5% paraformaldehyde and 0.1% glutaraldehyde and incubated with antibodies against CCM. Subcellular distributions of CCM are visualized by incubation with biotinylated goat anti-guinea pig IgG (Kirkegaard and Perry Laboratories, Gaithersburg Md.) followed by streptavidin complexed with the fluorescent dye Texas Red (APB).

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

| mean log2 DE (Cy5/Cy3) | CV % | Cy3 | Cy5 |
|---|---|---|---|
| −1.92 | 4.03 | Human, Colon Pool, Nrml, Dn3753 | Human, Colon Tumor, Cancer, Dn3311 |
| −1.87 | 5.44 | Human, Colon Pool, Nrml, Dn3753 | Human, Colon Tumor, Cancer, Dn3757 |
| −1.65 | 0 | Human, Colon Pool, Nrml, Dn3753 | Human, Colon Tumor, Cancer, Dn3756 |
| −1.61 | 18.65 | Human, Colon Pool, Nrml, Dn3753 | Human, Colon, Polyp, Dn3755 |
| −1.41 | 5.18 | Human, Colon Pool, Nrml, Dn3753 | Human, Colon, Polyp, Dn3754 |
| −2.29 | 6.8 | Human, Colon Pool, Nrml, mw/AdenoCA, Dn3649 | Human, Colon Tumor, AdenoCA, Dn3649 |
| −1.04 | 11.76 | Human, Colon Pool, Nrml, mw/Cancer, Dn3647 | Human, Colon Tumor, Cancer, Dn3647 |
| −0.84 | 1.41 | Human, Colon Pool, Nrml, mw/Adenoma, Dn3583 | Human, Colon Tumor, Adenoma, Dn3583 |
| 0.18 | 5.23 | Human, Colon, Mucosa, mw/AdenoCA, Dn3983 | Human, Colon, Polyp, mw/AdenoCA, Dn3983 |

What is claimed is:

1. An isolated cDNA encoding a protein comprising the amino acid sequence of SEQ ID NO:1.

2. An isolated cDNA selected from:
   a) a nucleic acid sequence of SEQ ID NO:2 or the complete complement;
   b) a fragment of SEQ ID NO:2 selected from SEQ ID NOs:3–22 or the complete complements thereof; and
   c) a variant of SEQ ID NO:2 selected from SEQ ID NOs:23–34.

3. A composition consisting of a cDNA or the complete complement of a cDNA encoding an amino acid sequence of SEQ ID NO:1.

4. A vector comprising the cDNA of claim 1.

5. A host cell comprising the vector of claim 4.

6. A method for using a cDNA to produce a protein of SEQ ID NO:1, the method comprising:
   a) culturing the host cell of claim 5 under conditions for protein expression; and
   b) recovering the protein from the host cell culture.

7. A method for using a cDNA to detect expression of a nucleic acid in a sample comprising:
   a) hybridizing the composition of claim 3 to nucleic acids of the sample, thereby forming hybridization complexes; and
   b) comparing hybridization complex formation with a standard, wherein the comparison indicates expression of the cDNA in the sample.

8. The method of claim 7 further comprising amplifying the nucleic acids of the sample prior to hybridization.

9. The method of claim 7 wherein the composition is attached to a substrate.

10. The method of claim 7 wherein the cDNA is differentially expressed when compared with the standard and diagnostic of colon disorders, particularly colon cancer and polyps.

* * * * *

SEQUENCE LISTING

<160> NUMBER OF SEQ ID NOS: 36

<210> SEQ ID NO 1
<211> LENGTH: 784
<212> TYPE: PRT
<213> ORGANISM: Homo sapiens
<220> FEATURE:
<221> NAME/KEY: misc_feature
<223> OTHER INFORMATION: Incyte ID No: 5098390CD1

<400> SEQUENCE: 1

```
Met Ala Ser Leu Asp Asp Pro Gly Glu Val Arg Glu Gly Phe Leu
  1               5                  10                  15

Cys Pro Leu Cys Leu Lys Asp Leu Gln Ser Phe Tyr Gln Leu His
                 20                  25                  30

Ser His Tyr Glu Glu Glu His Ser Gly Glu Asp Arg Asp Val Lys
                 35                  40                  45

Gly Gln Ile Lys Ser Leu Val Gln Lys Ala Lys Lys Ala Lys Asp
                 50                  55                  60

Arg Leu Leu Lys Arg Glu Gly Asp Asp Arg Ala Glu Ser Gly Thr
                 65                  70                  75

Gln Gly Tyr Glu Ser Phe Ser Tyr Gly Gly Val Asp Pro Tyr Met
                 80                  85                  90

Trp Glu Pro Gln Glu Leu Gly Ala Val Arg Ser His Leu Ser Asp
                 95                 100                 105

Phe Lys Lys His Arg Ala Ala Arg Ile Asp His Tyr Val Val Glu
                110                 115                 120

Val Asn Lys Leu Ile Ile Arg Leu Glu Lys Leu Thr Ala Phe Asp
                125                 130                 135

Arg Thr Asn Thr Glu Ser Ala Lys Ile Arg Ala Ile Glu Lys Ser
                140                 145                 150

Val Val Pro Trp Val Asn Asp Gln Asp Val Pro Phe Cys Pro Asp
                155                 160                 165

Cys Gly Asn Lys Phe Ser Ile Arg Asn Arg Arg His His Cys Arg
                170                 175                 180
```

```
Leu Cys Gly Ser Ile Met Cys Lys Lys Cys Met Glu Leu Ile Ser
            185                 190                 195

Leu Pro Leu Ala Asn Lys Leu Thr Ser Ala Ser Lys Glu Ser Leu
            200                 205                 210

Ser Thr His Thr Ser Pro Ser Gln Ser Pro Asn Ser Val His Gly
            215                 220                 225

Ser Arg Arg Gly Ser Ile Ser Ser Met Ser Ser Val Ser Ser Val
            230                 235                 240

Leu Asp Glu Lys Asp Asp Asp Arg Ile Arg Cys Cys Thr His Cys
            245                 250                 255

Lys Asp Thr Leu Leu Lys Arg Glu Gln Gln Ile Asp Glu Lys Glu
            260                 265                 270

His Thr Pro Asp Ile Val Lys Leu Tyr Glu Lys Leu Arg Leu Cys
            275                 280                 285

Met Glu Lys Val Asp Gln Lys Ala Pro Glu Tyr Ile Arg Met Ala
            290                 295                 300

Ala Ser Leu Asn Ala Gly Glu Thr Thr Tyr Ser Leu Glu His Ala
            305                 310                 315

Ser Asp Leu Arg Val Glu Val Gln Lys Val Tyr Glu Leu Ile Asp
            320                 325                 330

Ala Leu Ser Lys Lys Ile Leu Thr Leu Gly Leu Asn Gln Asp Pro
            335                 340                 345

Pro Pro His Pro Ser Asn Leu Arg Leu Gln Arg Met Ile Arg Tyr
            350                 355                 360

Ser Ala Thr Leu Phe Val Gln Glu Lys Leu Leu Gly Leu Met Ser
            365                 370                 375

Leu Pro Thr Lys Glu Gln Phe Glu Glu Leu Lys Lys Lys Arg Lys
            380                 385                 390

Glu Glu Met Glu Arg Lys Arg Ala Val Glu Arg Gln Ala Ala Leu
            395                 400                 405

Glu Ser Gln Arg Arg Leu Glu Glu Arg Gln Ser Gly Leu Ala Ser
            410                 415                 420

Arg Ala Ala Asn Gly Glu Val Ala Ser Leu Arg Arg Gly Pro Ala
            425                 430                 435

Pro Leu Arg Lys Ala Glu Gly Trp Leu Pro Leu Ser Gly Gly Gln
            440                 445                 450

Gly Gln Ser Glu Asp Ser Asp Pro Leu Leu Gln Gln Ile His Asn
            455                 460                 465

Ile Thr Ser Phe Ile Arg Gln Ala Lys Ala Ala Gly Arg Met Asp
            470                 475                 480

Glu Val Arg Thr Leu Gln Glu Asn Leu Arg Gln Leu Gln Asp Glu
            485                 490                 495

Tyr Asp Gln Gln Gln Thr Glu Lys Ala Ile Glu Leu Ser Arg Arg
            500                 505                 510

Gln Ala Glu Glu Glu Asp Leu Gln Arg Glu Gln Leu Gln Met Leu
            515                 520                 525

Arg Glu Arg Glu Leu Glu Arg Glu Arg Glu Gln Phe Arg Val Ala
            530                 535                 540

Ser Leu His Thr Arg Thr Arg Ser Leu Asp Phe Arg Glu Ile Gly
            545                 550                 555

Pro Phe Gln Leu Glu Pro Ser Arg Glu Pro Arg Thr His Leu Ala
            560                 565                 570
```

-continued

```
Tyr Ala Leu Asp Leu Gly Ser Ser Pro Val Pro Ser Ser Thr Ala
            575                 580                 585

Pro Lys Thr Pro Ser Leu Ser Ser Thr Gln Pro Thr Arg Val Trp
            590                 595                 600

Ser Gly Pro Pro Ala Val Gly Gln Glu Arg Leu Pro Gln Ser Ser
            605                 610                 615

Met Pro Gln Gln His Glu Gly Pro Ser Leu Asn Pro Phe Asp Glu
            620                 625                 630

Glu Asp Leu Ser Ser Pro Met Glu Glu Ala Thr Thr Gly Pro Pro
            635                 640                 645

Ala Ala Gly Val Ser Leu Asp Pro Ser Ala Arg Ile Leu Lys Glu
            650                 655                 660

Tyr Asn Pro Phe Glu Glu Asp Glu Glu Glu Ala Val Ala
            665                 670                 675

Gly Asn Pro Phe Ile Gln Pro Asp Ser Pro Ala Pro Asn Pro Phe
            680                 685                 690

Ser Glu Glu Asp Glu His Pro Gln Gln Arg Leu Ser Ser Pro Leu
            695                 700                 705

Val Pro Gly Asn Pro Phe Glu Pro Thr Cys Ile Asn Pro Phe
            710                 715                 720

Glu Met Asp Ser Asp Ser Gly Pro Glu Ala Glu Pro Ile Glu
            725                 730                 735

Glu Glu Leu Leu Leu Gln Gln Ile Asp Asn Ile Lys Ala Tyr Ile
            740                 745                 750

Phe Asp Ala Lys Gln Cys Gly Arg Leu Asp Glu Val Glu Val Leu
            755                 760                 765

Thr Glu Asn Leu Arg Glu Leu Lys His Thr Leu Ala Lys Gln Lys
            770                 775                 780

Gly Gly Thr Asp
```

<210> SEQ ID NO 2
<211> LENGTH: 8021
<212> TYPE: DNA
<213> ORGANISM: Homo sapiens
<220> FEATURE:
<221> NAME/KEY: misc_feature
<223> OTHER INFORMATION: Incyte ID No: 5098390CB1

<400> SEQUENCE: 2

```
gcctgccgag ttccgagcga ccgatggaga tggcggctgc ggctgagtga cggacggtgg      60
aggcccagag cccgggcctg aaggggggga caaacctggg tgcccgcagg agcccggcag     120
ggtgtcttac aagtatcaag aacttactat atgtggttga ataaacaatc aaggtaaaga     180
gcatcaagta aaaacttctg cttgttgata agtacttcag acattccccc agtggctgaa     240
gtggcatatg aattatgaag ttggatcatt tggaatgaat gtaagagaat tgccaagggc     300
tcctcctact ccagagagga aacctcatcc agggccatga agccacttcc tcaccatctg     360
tgtgctgctt aagctaatgc tgcgggaacc atggttcctt ggaggaatc aagctgactc      420
ttggcatgag attcctgcct tcctagggtt gagagcggca ctgccatggc ttctctggac     480
gacccagggg aagtgaggga gggcttcctc tgccctctgt gcctgaagga tctgcagtct     540
ttctatcagc ttcactcaca ttacgaggaa gaacactcag gggaagaccg tgatgtcaaa     600
gggcaaatta aaagtcttgt ccagaaggct aaaaaagcaa aggacaggtt gttgaaacga     660
gaaggggatg atcgagcaga gtcagggacc caaggatatg agtctttcag ctatggaggg     720
```

-continued

| | |
|---|---|
| gttgatcctt acatgtggga accccaggag cttggtgctg tgagaagcca tctttccgac | 780 |
| ttcaaaaaac accgagctgc tagaattgac cactatgttg tggaagtcaa taaactaata | 840 |
| atcaggttag agaagctcac tgcatttgac agaacaaata ctgagtctgc aaagattcga | 900 |
| gcaatagaaa agtctgtggt gccttgggtc aacgaccagg atgtcccttt ctgtccagac | 960 |
| tgtgggaata agttcagcat ccggaaccgc cgccaccact gccgcctctg cgggtctatt | 1020 |
| atgtgcaaga agtgtatgga gctcatcagc cttcccttgg caaacaagct caccagtgcc | 1080 |
| agcaaggagt ccctgagcac ccacaccagc cccagccagt cacccaacag tgtccatggc | 1140 |
| tcccgccgag gcagcatcag cagcatgagc agtgtcagct cggtcctgga tgagaaggac | 1200 |
| gatgaccgga tccgctgctg tacacactgc aaggacacgc tgctcaagag agagcagcag | 1260 |
| attgatgaga aggagcacac acctgacatc gtgaagctct acgagaaatt acgactttgc | 1320 |
| atggagaaag ttgaccagaa agctccagaa tacatcagga tggcagcatc attaaatgct | 1380 |
| ggggagacaa cctacagtct ggaacatgcc agtgaccttc gagtggaagt gcagaaagtg | 1440 |
| tatgagctga tagcgctttt aagtaagaag atcttaacct tgggcttgaa ccaggaccct | 1500 |
| ccaccacatc caagcaattt gcggctgcag agaatgatca gatactcagc tacactttttt | 1560 |
| gtgcaggaaa agttgcttgg tttgatgtca ctgccaacca aagaacagtt tgaggaactg | 1620 |
| aaaaagaaaa ggaaggagga aatggagagg aagagggccg tggagagaca agctgccctg | 1680 |
| gagtcccagc gaaggcttga ggaaaggcag agtggcctgg cttctcgagc ggccaacggg | 1740 |
| gaggtggcat ctctccgcag gggccctgcc cccttgagaa aggctgaggg ctggctccca | 1800 |
| ctgtcaggag gtcaggggca gagtgaggac tcagacccgc tcctccagca gatccacaac | 1860 |
| atcacatcat tcatcaggca ggccaaggcc gcgggccgca tggatgaagt gcgcactctg | 1920 |
| caggagaacc tgcggcagct gcaggacgag tatgaccagc agcagacaga gaaggccatc | 1980 |
| gagctgtccc ggaggcaggc tgaggaggag gacctgcagc gggaacagct gcagatgttg | 2040 |
| cgtgaacggg agttggaacg agaaagggag cagtttcggg tggcatccct gcacacacgg | 2100 |
| actcggtccc tggacttcag agaaatcggc ccttttcagc tggagcccag cagagagcct | 2160 |
| cgcacccacc ttgcttatgc tttggatcta ggctcttccc cagttccaag cagcacagct | 2220 |
| cccaagaccc cttcacttag ctcaactcaa cccaccagag tgtggtctgg cccccagcc | 2280 |
| gttggccagg agcgcttacc ccagagcagc atgccacagc aacatgaggg gccctcctta | 2340 |
| aaccctttg atgaggaaga cctctccagc cccatggaag aggccactac tggtcctcct | 2400 |
| gctgcagggg tttccttaga cccttcagcc cgcatcctga agagtacaa tcctttcgag | 2460 |
| gaagaggacg aggaggagga agcagtggca gggaatccat tcattcagcc agacagccca | 2520 |
| gctcctaacc ccttcagtga ggaagacgaa catccccagc agaggctctc aagccctctg | 2580 |
| gttcctggta accccttttga ggaacccacc tgtatcaacc cctttgagat ggacagtgac | 2640 |
| agtgggccag aggctgagga gcccatagag gaagagctcc tcctgcagca gatcgataac | 2700 |
| atcaaggcat acatctttga tgccaagcag tgcggccgcc tggatgaggt agaggtgctg | 2760 |
| acagagaatc tgcgggagct gaagcacacc ctggccaagc agaaggggg cactgactga | 2820 |
| ccagcagtgg agagggcacc tttgggccca ggggtctggc aggagccagt ggagcaggac | 2880 |
| agagggcagg caggatggat ggggaaggtg gcagggtgag aactcagatg cacacaggtg | 2940 |
| aggggcagga atctgctgtt ttgtgttgcg cactttgagg tatttccact acagttgaat | 3000 |
| aataaaatag aaactagaac aggagagaatc agcattcagt tgctgctttt cctgtttatt | 3060 |
| attactatct tttgtaatcg gaggtttacc ccttttgaag ggactttaca tttttactac | 3120 |

-continued

```
cgagatataa ctaaatgcag ctctgttggg cccagggcag aaatggctgc tgtgtacctc    3180
ttgggtccat ttgctactgc ctagtcttgg ttccttatgc agtattatag ggcagccttt    3240
ttagagccct tcctttagcc aagacagaga agatagattc cactgagctc tattctgctc    3300
tgacagaagt ccatccctag taggctgtga gttccatttc acctgggccc gcctctcccc    3360
tgctctgcac ttcctgtctg tacaatagaa gggggaggtg ctgctatgaa ggggagagtt    3420
tagacccagg agagcccagc acctctcttt aaggtggggt gatgggaata tttcaccagg    3480
gtctattttc tcagtttaag ttcttttttg tctctttcag gaagttaagc tcccagtgca    3540
gggtatcaat gtgaatctgg tcctgagctt tttagaaaat aagagtggtg gccgggcgcg    3600
ctggctcacg cctgtaatcg caacactttg ggaggccgag gcaggcagat cacaaggtca    3660
ggagatcgag accaccctgg ctaacacagt gaaatcccgt ctctactaaa aatacaaaaa    3720
attagccagg cgtggtggtg ggtgcctgtg gtcccggcta ctttggaggc tgaggcagga    3780
gaatgctgtg aacccgggag gcagagcttg cagtgggccg agatcgcacc actgcactcc    3840
agcctgggca gtgagagtga gactccgtct caaaaaaaaa taagagtggt taacttttgt    3900
gttgatatta gtattatttg tgagaagagt ttccccaccc ttcttctgat agaacaattg    3960
tctgtcactg gagaaatctc cctccagagc tttggcaaag ttactctgat ctgggtctgt    4020
ttaaaaggcc gggtctctaa tttaggaatc ggtgatttgg aagcttttgc agaacatcac    4080
cagaagaagg gaagcttccc agagtcagaa gctaaattaa aataatttcc aaggctattt    4140
gatcagcctt cttccttttt ggttcattgt gtcctgactt ggggcactga tgagattttt    4200
tatttttttt gagacggagt ttcactttgt tgcccaggct ggagtgtagt ggcatgatct    4260
cggctcactg caacctccac ctccctggtt caagtgatat ttgtgcctca gcccctgaa    4320 tagctgggat tacaggcgtg gccaccacg cctggttaat tctgtatttt ttggtagagg    4380
tagagtttca ccattttggc caggctggtt tcgaactcct ggcctcaagt gatctgccac    4440
cttggcctcc caaagtgctg ggaatacagg cgtgagccac tgtgcccgcc ctgatgagat    4500
attttattac caatgttagt attgagaaac tgaaatgttt gaagaagcac aacccaggat    4560
cgtgctggta gcaccacagt acttaaactg ttggtcaatt aaggccagaa agggaaattg    4620
ttaatttagc tctggtgctt tggtttacag gaacataact cttaactgac atctgacatc    4680
atgatagcca tatgtgctca gctctgggta gagtttctgc agttactcat ctgaactaat    4740
gaacaataac tgaccactag tcactttatg ccgtgtaact agctctaggc catactttca    4800
ctggttactg gtgtgaaagc tgaaattcat tttgttacat tctggtgaag accccctcttg    4860 ataatgggaa tgttttaact ctcttgatga aaaataatc tgtatttgtg ttgatgttca    4920
catttctgta gcacatttct tatccttttg gttgaatgaa aagatcttgt ataggggtgt    4980
ggagatgggg agtgggtaga agtgtgtgaa ggacgctttg catttgggat ctgttcacaa    5040
acagccatat gagtgtgtta atgaatgtca gccagttacc aaccctgctg gttgttatgg    5100
gttgttttga gaagttggca accaggcatc taagatgttg cctggtacag gcctcttttc    5160
ttccctgagg cccatgacat ttctctgtta ctctagaggg ttttctcagat ggccagtagg    5220 ctcctccctg cttagggtct catttctctg aaaagaggat gaactgaaaa gcaggtagtt    5280
ccagaagcta attgctgctt tccatcataa ttatttttct tgtgagaaca tttctctttt    5340
aattagctag tgattttgat taagactaat tcactaaaca tacccttccc tcaaatcacc    5400
tcaggtagca atctgtaagt aactaaaagc attgaaaaac acacaagaaa catttttaaa    5460
```

```
aactattttt aaaggcctgg ccgggtgcag tggctcactc ctgtaatccc agcactttgg   5520
gaggccgaga cgggtggatc acctgaggtc aggaatttga gactagcatg gccaacatgg   5580
tgaaaccccg tgtctactaa aaatacaaaa attagctggg cgtggtggca gacgcctgta   5640
atcccagcta ctcagggagg ctgaggcacg agaatcgctt gaacctggga ggcggaggtt   5700
gcagtgagcc aagattgcgc cactgcactc caacctgggt gacaagagca agactccgtc   5760
tcacaaaaaa caaacaaaac tgactgattg aatatactaa accaaactaa atcatattc    5820
ttttgattaa gtttatccat ggctgtattc ttctatgaat tcttccattt aattcttcca   5880
cgattatctt ctcctgtaaa tacatcacag gagttagaat tctctaccca tcagctgtac   5940
catgtcgcag aattcatgca ggcacaaagt tggagttaca gagatgggtt gacagcaggc   6000
aaacttggcc tatgtattat aaccacaact tcaagttctt acctcatgtg aatattcacc   6060
ctttctttag tcttccaagg caaacagccc cgtctcatca ccagatgagc aaggtcttga   6120
tatggcatag cagatctccc tagacacaga tcatgagaaa agatggaaga gacttaggga   6180
ttcaggcatc agatgaagtt ggcttttccc ttttatgcct tgtttgtatt taccctgtct   6240
aatacactaa ggatacttac tcattgtact tgcagctcaa tatgtctttg ctgttcagat   6300
actaaaatgt acctctgagt cattgtgagc tgtgtggtag gttggacatt ggcatagttg   6360
gtgatgggac tcaaaatgaa aagtggtct ctttaccagg tcacagactg tagcagattg    6420
tgcttgttat ctgacaatga ctgtcacttt gagggtcgtt gatttgcatg cactactctg   6480
gggccttgta ttggagcctt ttttaaaaaa aataaaatct gagatagagg ttgggggtgt   6540
gtgtgtctgt gtgcacatgt gttacaagtg agaatcatca gatgacatcc cttctccttt   6600
cttgatgaca accatctgag tatcagaata gttccagcac ctgtgttgtt tgtctggtta   6660
aggcctctgg aaaaaatgaa ggtcactggg ttctgaacag gggatagata cgggttccag   6720
ttctgcccctt attcccagtt attcctgcag tgctggttaa atgaacagtt ttacagaagt   6780
atagtgcaga tcccttaatg atcctatcat cccagtttca cactggaaga aactgaggct   6840
cagagattga ggaaccttgt gactgccatc tgtgccagtc accacctctg catgaccaca   6900
tttccctcca ttagcactac cagcatgcct gtgaggtagt tactcagctg ttcatctgac   6960
cccagacgta gaaaagttaa gagagattag cctggcttag gccacacagc cagtcagtgg   7020
tggaatgagg gtttaaatcc agatctgcct gacttaattt gccctcagta ataagtagct   7080
gggtcaggta gtggtgtggt ggtggtgggt gctcaaccat tgtgtcaagc tcaaagaggg   7140
cagaaaaggg caatggggaa tgaggttggg tgctgctgag ctggtttccg atagtgactg   7200
cctgagtctg tgaaactgag acctccttag ggccttaaga atatatagat tcttaaacca   7260
ggagagtata atatctagtg ctcactgtag gctagactga gtgctaagta ttacgcatgg   7320
cttacctcag tcttcccaac aacccattta cacatgcaga aatgagtgag tggtgaagtt   7380
aagcttgctt agggttgcac tgctgggttt ccagcctagg tctgtctgac tgcaaaaccc   7440
aagctgccct agattgtgtt gtatgtgac acccatgttt ctaatgtgga atggggtgtt    7500
tcatccctag caagtgcctc ctgtggactt ttaagatgaa aaacttctgc ctaactcttc   7560
aggaagccta gcgtagttgt aaaaatactt cagaaagcac ttctggtttt agctcagaca   7620
cgtagagttt gaaagttatc ctatccttac cacaagaaaa agctgggcaa actcaaaagc   7680
attggccttt cttggtccca ttagagagct gagtgtgcag gtcaaactgc catcccaaaa   7740
tctagagaga ggtgagtcca gagagtgagc aagatctaat tgcctggagc agaagccacg   7800
ggagccatag ctagtaggaa aacttaaatg gtaattttga tgaactgctg gaggttgagt   7860
```

```
gtggactagc atgggaggga gcaactcccc ctcaccccca acgctttcct gggttttacc      7920
ctacttggtt ctattggtga agagctgagg aagaccctct ggtgactctg gcaggggaaa      7980
gggagaatca tctttgtaat cagagccttc tccataataa a                          8021

<210> SEQ ID NO 3
<211> LENGTH: 432
<212> TYPE: DNA
<213> ORGANISM: Homo sapiens
<220> FEATURE:
<221> NAME/KEY: misc_feature
<223> OTHER INFORMATION: Incyte ID No: 5098390F6

<400> SEQUENCE: 3
gcagagagcc tcgcacccac cttgcttatg ctttggatct aggctcttcc ccagttccaa        60
gcagcacagc tcccaagacc ccttcactta gctcaactca acccaccaga gtgtggtctg       120
ggcccccagc cgttggccag gagcgcttac cccagagcag catgccacag caacatgagg       180
ggccctcctt aaacccctt gatgaggaag acctctccag ccccatggaa gaggccacta       240
ctggtcctcc tgctgcaggg gtttccttag acccttcagc ccgcatcctg aaagagtaca       300
atcctttcga ggaagaggac gaagaggagg aagcagtggc agggaatcca ttcattcagc       360
cagacagccc agctcctaac cccttcagtg agggaagacg aacatcccca gcagaggctc       420
tcaagccctc tg                                                            432

<210> SEQ ID NO 4
<211> LENGTH: 573
<212> TYPE: DNA
<213> ORGANISM: Homo sapiens
<220> FEATURE:
<221> NAME/KEY: misc_feature
<223> OTHER INFORMATION: Incyte ID No: 8022266J1

<400> SEQUENCE: 4
gcctgccgag ttccgagcga ccgatggaga tggcggctgc ggctgagtga cggacggtgg        60
aggcccagag cccgggcctg aaggggggga caaacctggg tgcccgcagg agcccggcag       120
ggtgtcttac aagtatcaag aacttactat atgtggttga ataaacaatc aaggtaaaga       180
gcatcaagta aaaacttctg cttgttgata agtacttcag acattccccc agtggctgaa       240
gtggcatatg aattatgaag ttggatcatt tggaatgaat ggctcctcct actccagaga       300
ggaaacctca tccagggcca tgaagccact tcctcaccat ctgtgtgctg cttaagctaa       360
tgctgcggga accatggttc cttgggagga atcaagctga ctcttggcat gagattcctg       420
ccttcctagg gttgagagcg gcactgccat ggcttctctg gacgacccag gggaagtgag       480
ggagggcttc ctctgccctc tgtgcctgaa ggatctgcag tctttctatc agcttcactc       540
acattacgag gaagaacact cagggaaga ccg                                    573

<210> SEQ ID NO 5
<211> LENGTH: 598
<212> TYPE: DNA
<213> ORGANISM: Homo sapiens
<220> FEATURE:
<221> NAME/KEY: misc_feature
<223> OTHER INFORMATION: Incyte ID No: 7394066H1

<400> SEQUENCE: 5
actgctcatg ctgctgatgc tgcctcggcg ggagccatgg acactgttgg gtgactggct        60
ggggctggtg tgggtgctca gggactcctt gctggcactg gtgagcttgt ttgccaaggg       120
```

-continued

```
aaggctgatg agctccatac acttcttgca cataatagac ccgcagaggc ggcagtggtg      180
gcggcggttc cggatgctga acttattccc acagtctgga cagaaaggga catcctggtc      240
gttgacccaa ggcaccacag acttttctat tgctcgaatc tttgcagact cagtatttgt      300
tctgtcaaat gcagtgagct tctctaacct gattattagt ttattgactt ccacaacata      360
gtggtcaatt ctagcagctc ggtgtttttt gaagtcggaa agatggcttc tcacagcacc      420
aagctcctgg ggttcccaca tgtaaggatc aaccoctcca tagctgaaag actcatatcc      480
ttgggtccct gactctgctc gatcatcccc ttctcgtttc aacaactgtc ctttgctttt      540
ttagccttct ggacaagact tttaatttgc ctttgacatc acggtcttcc cctgagtg       598
```

<210> SEQ ID NO 6
<211> LENGTH: 595
<212> TYPE: DNA
<213> ORGANISM: Homo sapiens
<220> FEATURE:
<221> NAME/KEY: misc_feature
<223> OTHER INFORMATION: Incyte ID No: 6309461H1

<400> SEQUENCE: 6

```
atggtcttgt tagatcttca ctgcacctca tgagaacctg cccagggaca aacagtgctg      60
tgagaagcca tctttccgac ttcaaaaaac accgagctgc tagaattgac cactatgttg      120
tggaagtcaa taaactaata atcaggttag agaagctcac tgcatttgac agaacaaata      180
ctgagtctgc aaagattcga gcaatagaaa agtctgtggt gccttgggtc aacgaccagg      240
atgtcccttt ctgtccagac tgtgggaata agttcagcat ccggaaccgc cgccaccact      300
gccgcctctg cgggtctatt atgtgcaaga agtgtatgga gctcatcagc cttcccttgg      360
caaacaagct caccagtgcc agcaaggagt ccctgagcac ccacaccagc ccagccagt      420 cacccaacag tgtccatggc tcccgccgag gcagcatcag cagcatgagc agtgtcagct      480
cggtcctgga tgagaaggac gatgaccgga tccgctgctg tacacactgc aaggacacgc      540
tgctcaagag agagcagccg attgatgaga aggagccaca cctgaacatc gtgaa           595
```

<210> SEQ ID NO 7
<211> LENGTH: 645
<212> TYPE: DNA
<213> ORGANISM: Homo sapiens
<220> FEATURE:
<221> NAME/KEY: misc_feature
<223> OTHER INFORMATION: Incyte ID No: 7436032H1
<221> NAME/KEY: unsure
<222> LOCATION: 20
<223> OTHER INFORMATION: a, t, c, g, or other

<400> SEQUENCE: 7

```
tgcactcata taggcgccan tgggctcact acatgcatgc tcgagcggcc gccagtgtgc      60
tggaaagtct gtggtgcctt gggtcaacga ccaggatgtc cctttctgtc cagactgtgg      120
gaataagttc agcatccgga accgccgcca ccactgccgc ctctgcgggt ctattatgtg      180
caagaagtgt atggagctca tcagccttcc cttggcaaaa attacgactt tgcatggaga      240
aagttgacca gaaagctcca gaatacatca ggatggcagc atcattaaat gctggggaga      300
caacctacag tctggaacat gccagtgacc ttcgagtgga agtgcagaaa gtgtatgagc      360
tgatagacgc tttaagtaag aagatcttaa ccttgggctt gaaccaggac cctccaccac      420
atccaagcaa tttgcggctg cagagaatga tcagatactc agctacactt tttgtgcagg      480
aaaagttgct tggtttgatg tcactgccaa ccaaagaaca gtttgaggaa ctgaaaaaga      540
```

```
aaaggaagga ggaaatggag aggaagaggg ccgtggagag acaagctgcc ctggagtccc      600
agcgaaggct tgaggaaagg cagagtgggc tggcttctcg agcgg                      645
```

<210> SEQ ID NO 8
<211> LENGTH: 611
<212> TYPE: DNA
<213> ORGANISM: Homo sapiens
<220> FEATURE:
<221> NAME/KEY: misc_feature
<223> OTHER INFORMATION: Incyte ID No: 7676140H2

<400> SEQUENCE: 8

```
tataactcat atagggcgca tggggcctct agatgcatgc tcgaagcggc cgccagtgtg       60
ctggaaagta aacggagtc tcactctgtt gccaggctgg agtgcagtgg cgtgatctcg       120
gctcactgtg acctccacct cccagtgctg ggagacaac ctacagtctg aacatgcca       180 gtgaccttcg agtggaagtg cagaaagtgt atgagctgat agacgcttta agtaagaaga      240
tcttaacctt gggcttgaac caggaccctc caccacatcc aagcaatttg cggctgcaga      300
gaatgatcag atactcagct cacttttg tgcaggaaaa gttgcttggt ttgatgtcac        360
tgccaaccaa agaacagttc gaggaactga aaaagaaaag gaaggaggaa atggagagga      420
agagggccgt ggagagacaa gctgccctgg agtcccagcg aaggcttgag gaaaggcaga      480
gtggcctggc ttctcgagcg gccaacgggg aggtggcatc tctccgcagg ggccctgccc      540
ccttgagaaa ggctgagggc tggctcccac tgtcaggagg tcaggcgcag agtgaggact      600
cagacccgct c                                                          611
```

<210> SEQ ID NO 9
<211> LENGTH: 556
<212> TYPE: DNA
<213> ORGANISM: Homo sapiens
<220> FEATURE:
<221> NAME/KEY: misc_feature
<223> OTHER INFORMATION: Incyte ID No: 6923049H1

<400> SEQUENCE: 9

```
ggcatctctc cgcaggggcc ctgccccctt gagaaaggct gagggctggc tcccactgtc       60
aggaggtcag gcgcagagtg aggactcaga cccgctcctc cagcagatcc acaacatcac      120
atcattcatc aggcaggcca aggccgcggg ccgcatggat gaagtgcgca ctctgcagga      180
gaacctgcgg cagctgcagg acgagtatga ccagcagcag acagagaagg ccatcgagct      240 gtcccgagg caggctgagg aggaggacct gcagcgggaa cagttgcaga tgttgcgtga      300
acgggagtgg gaacgagaaa gggagcagtt tcgggtggca tccctgcaca cacggactcg      360
gtccctggac ttcagagaaa tcgcgccttt tcagctggag cccagcagag agcctcgcac      420
ccaccttgct tatgcttggg atctaggctc ttccccagtt cccagcagca cagttcccaa      480 gaaccttca gttagctcaa gtcaacccac cagagtgttg tctgggcccc agccgttggc      540
aggagcgctt accca                                                      556
```

<210> SEQ ID NO 10
<211> LENGTH: 915
<212> TYPE: DNA
<213> ORGANISM: Homo sapiens
<220> FEATURE:
<221> NAME/KEY: misc_feature
<223> OTHER INFORMATION: Incyte ID No: 8216794J1

<400> SEQUENCE: 10

```
gatagcagtc taatagactc actatatgga aagctggtac gcctgcaggt accggtccgg     60
aattacttcc cgggtcgacg agctcactag tcggcggcgc actgcttggc atcaaagatg    120
tatgccttga tgttatcgat ctgctgcagg aggagctctt cctctatggg ctcctcagcc    180
tctggcccac tgtcactgtc catctcaaag gggttgatac aggtgggttc ctcaaagggg    240
ttaccaggaa ccagagggct tgagagcctc tgctgggat gttcgtcttc ctcactgaag     300
gggttaggag ctgggctgtc tggctgaatg aatggattcc ctgccactgc ttcctcctcc    360
tcgtcctctt cctcgaaagg attgtactct ttcaggatgc gggctgaagg gtctaaggaa    420 accctgcag caggaggacc agtagtggcc tcttccatgg ggctggcaga ggtcttcctc     480
atcaaagggg tttaaggagg gcccctcatg ttgctgtggc atgctgctct ggggtaagcg    540
ctcctggcca acggctgggg cccagaccac actctggtgg gttgagttga gctaagtgaa    600
ggggtcttgg gagctgtgct gcttgtaact ggggaagagc ctagatccaa agcataaagc    660
aaggtgggtg cgaggctctc tgctgggtct ccagctgaaa aggggcgatt tctctgaagt    720
ccaggaccga gtccgtgtgt gtcagggatg ccaccgaact gtcctttctc gttccaactc    780
cgttcacgca catctgaggc tgttcccgtg cggtctctct cagctgctcg gggaaggttc    840
gtggctttct ggtctgctgc tggtcttatc ttctgggttg ccgggtttct tggaggggcg    900 cttttttcacg tgggc                                                   915

<210> SEQ ID NO 11
<211> LENGTH: 552
<212> TYPE: DNA
<213> ORGANISM: Homo sapiens
<220> FEATURE:
<221> NAME/KEY: misc_feature
<223> OTHER INFORMATION: Incyte ID No: 6995895H1
<221> NAME/KEY: unsure
<222> LOCATION: 539, 542
<223> OTHER INFORMATION: a, t, c, g, or other

<400> SEQUENCE: 11
cctgttctag tttctatttt attattcaac tgtagtggaa atacctcaaa gtgcgcaaca     60 caaacagca gattcctgcc cctcacctgt gtgcatctga ttctcaccc tgccaccttc      120 cccatccatc ctgcctgccc tctgtcctgc tccactggct cctgccagac ccctgggccc    180
aaaggtgccc tctccactgc tggtcagtca gtgccccct tctgcttggc cagggtgtgc     240
ttcagctccc gcagattctc tgtcagcacc tctacctcat ccaggcggcc gcactgcttg    300
gcatcaaaga tgtatgcctt gatgttatcg atctgctgca ggaggagctc ttcctctatg    360
ggctcctcag cctctggccc actgtcactg tccatctcaa aggggttgat acaggtgggt    420
tcctcaaagg ggttaccagg aaccagaggg cttgagagcc tctgctgcgg atgttcctct    480
tcctcactga aggggttagg agctgagctg tctggctgaa tgaatggatt ccctgccant    540
gnttcctcct cc                                                       552

<210> SEQ ID NO 12
<211> LENGTH: 539
<212> TYPE: DNA
<213> ORGANISM: Homo sapiens
<220> FEATURE:
<221> NAME/KEY: misc_feature
<223> OTHER INFORMATION: Incyte ID No: 6889439H1

<400> SEQUENCE: 12
ggcactgact gaccagcagt ggagagggca cctttgggcc caggggtctg gcaggagcca     60
```

-continued

```
gtggagcagg acagagggca ggcaggatgg atggggaagg tggcagggtg agaactcaga    120
tgcacacagg tgaggggcag gaatctgctg ttttgtgttg cgcactttga ggtatttcca    180
ctacagttga ataataaaat agaaactaga acagggagaa tcagcattca gttgctgctt    240
ttcctgttta ttattactat cttttgtaat cggaggttta cccctttga agggacttta     300 cattttact accgagatat aactaaatgc agctctgttg ggcccagggc agaaatggct     360
gctgtgtacc tcttgggtcc atttgctact gcctagtctt ggttccttat gcagtattat    420
agggcagcct ttttagagcc cttcctttag ccaagacaga gaagatagat tccactgagc    480
tctattctgc tctgacagaa gtccatccct agtaggctgt gagttccatt tcacctggg    539
```

<210> SEQ ID NO 13
<211> LENGTH: 409
<212> TYPE: DNA
<213> ORGANISM: Homo sapiens
<220> FEATURE:
<221> NAME/KEY: misc_feature
<223> OTHER INFORMATION: Incyte ID No: 70405975D1

<400> SEQUENCE: 13

```
ctactgtgta cctcttgggt ccatttgcta ctgcctagtc ttggttcctt atgcagtatt     60 ataggggcagc cttttagag cccttccttt agccaagaca gagaagatag attccactga    120
gctctattct gctctgacag aagtccatcc ctagtaggct gtgagttcca tttcacctgg    180
ggccgcctct cccctgctct gcacttcctg tctgtacaat agaagggga ggtgctgcta    240 tgaaggggag agtttagacc caggagagcc cagcacctct ctttaaggtg gggtgatggg    300
aatatttcac cagggtctat tttctcagtt taagttcttt tttgtctctt tcaggaagtt    360
aagctcccag tgcagggtat caatgtgaat ctggtcctga gctttttag               409
```

<210> SEQ ID NO 14
<211> LENGTH: 698
<212> TYPE: DNA
<213> ORGANISM: Homo sapiens
<220> FEATURE:
<221> NAME/KEY: misc_feature
<223> OTHER INFORMATION: Incyte ID No: 8117068H1

<400> SEQUENCE: 14

```
tacgcctgca ggtaccggtc cgtgaattcc cgggtcgacg gggggaggtg ctgctatgaa     60
ggagagagtt tagacccagg agagcccagc acctcttttt aaggtggggt gatgggaata    120
tttcaccagg ctctattttc tcagtttaag ttcttttttg tctctttcag gaagttaagc    180
tcccagtgca gggtatcaat gtgaatctgg tcctgagctt tttagaaaat aagagtggtg    240
gccgggcgcg ctggctcacg cctgtaatcg caacactttg ggaggccgag gcaggcagat    300
cacaaggtca ggagatcgag accaccctgg ctaacacagt gagatcccgt ctctgctgaa    360
aatacaaaaa attagccagg cgtgtgtggt gggtgcctgt ggtcccagct actttggagg    420
ctgaggcagg agaatgctgt gaacccggga ggcggagctt gcagtgagcc gagatcgcac    480
cactgtcact ccagcctggg cagtgagagt gagactccgt ctctaaaaaa aaataagagt    540
ggttaacttt ttggttgata ttagtattat ttgtgagaag agtttcccac cttcttctga    600
tagaacaatt gtctgtcact ggagaaatct tcctcagagc tttggcaagg ttctctgatc    660
tgggtctgtt taaaggccgg gtctctatta ggatcgga                           698
```

<210> SEQ ID NO 15

<210> SEQ ID NO 15
<211> LENGTH: 172
<212> TYPE: DNA
<213> ORGANISM: Homo sapiens
<220> FEATURE:
<221> NAME/KEY: misc_feature
<223> OTHER INFORMATION: Incyte ID No: 747646H1
<221> NAME/KEY: unsure
<222> LOCATION: 171
<223> OTHER INFORMATION: a, t, c, g, or other

<400> SEQUENCE: 15

```
gtggttaact ttttggttga tattagtatt atttgtgaga agagtttccc caccttctt      60
ctgatagaac aattgtctgt cactggagaa atctccctcc agagctttgg caaagttact    120
ctgatctggg tctgtttaaa aggccgggtc tctaatttag gaatcggtga nt            172
```

<210> SEQ ID NO 16
<211> LENGTH: 696
<212> TYPE: DNA
<213> ORGANISM: Homo sapiens
<220> FEATURE:
<221> NAME/KEY: misc_feature
<223> OTHER INFORMATION: Incyte ID No: 7984383H1

<400> SEQUENCE: 16

```
tgctggtacg cctgcaggta cggtccggaa ttcccgggtc gacggagga atcggtgatt     60
tggaagcttt tgcagaacat caccagaaga agggaagctt cccagagtca gaagctaaat   120
taaataatt tccaaggcta tttgatcagc cttcttcctt tttggttcat tgtgtcctga    180
cttggggcac tgatgagatt ttttattttt tttgagacgg agtttcactt tgttgcccag   240
gctggagtgt agtggcatga tctcggctca ctgcaacctc cacctccctg gttcaagtga   300
tatttgtgcc tcagccccct gaatagctgg gattacaggc gtgggccacc acgcctggtt   360
aatctctgta ttttttggtag aggtagagtt tcaccatttt ggccaggctg gtttcgaact   420
cctggcctca agtgatctgc caccttggcc tcccaaagtg ctgggaatac aggcgtgagc    480
cactgtgccc gccctgatga gatattttat taccaatgtt agtattgaga aactgaaatg    540
tttgaagaag cacaaccagg atcgtgctgg tagcaccaca gtacttaaac tggttggtca    600
attaaggcca gaaagggaaa tcgtgtattt agctctggtg ctttggttta caggaacata    660
actcttaagt gacatctggc gtttgataag ccattt                              696
```

<210> SEQ ID NO 17
<211> LENGTH: 711
<212> TYPE: DNA
<213> ORGANISM: Homo sapiens
<220> FEATURE:
<221> NAME/KEY: misc_feature
<223> OTHER INFORMATION: Incyte ID No: 8073132J1

<400> SEQUENCE: 17

```
agtgtgctgg aaccgattat gtatggaaag cagcaattag cttctggaac tacctgcttt     60
tcagttcatc ctcttttcag agaaatgaga ccctaagcag ggaggagcct actggccatc   120
tgagaaaccc tctagagtaa cagagaaatg tcatgggcct cagggaagaa aagaggcctg   180
taccaggcaa catcttagat gcctggttgc caacttctca aaacaaccca taacaaccag   240
cagggttggt aactggctga cattcattaa cacactcata tggctgtttg tgaacagatc   300
ccaaatgcaa agcgtccttc acacacttct acccactccc catctccaca ccctataca   360
agatcttttc attcaaccaa aaggataaga aatgtgctac agaaatgtga acatcaacac   420
aaatacagat tatttttttca tcaagagagt taaaacattc ccattatcaa gagggtctt    480
```

```
caccagaatg taacaaaatg aatttcagct ttcacaccag taaccagtga agtatggcc      540 tagagctagt tacacggcat aaagtgacta gtggtcagtt attgttcatt cagttcagat     600
gagtaactgc agaaactcta cccagaggct gagcacatat gggctatcat gatgtcggat    660
gtccgttaag agtaatgttc ctgtaacaaa agcaccagag ctaattacat t              711

<210> SEQ ID NO 18
<211> LENGTH: 528
<212> TYPE: DNA
<213> ORGANISM: Homo sapiens
<220> FEATURE:
<221> NAME/KEY: misc_feature
<223> OTHER INFORMATION: Incyte ID No: 6744627H1

<400> SEQUENCE: 18
gatttgtgta gatgttcaca tttctgtagc acagtttctt atccttttgg ttgaatgaaa     60
agatcttgta tagggtgtgt gagatgggga gtgggtagaa gtgtgtgaag gacgctttgc    120
atttgggatc tgtacacaaa cagccatatg agtgtgttaa tgaatgtcag ccagttacca    180
accctgctgg ttgttatggg ttgttttgag aagttggcaa ccaggcatct aagatgttgc    240
ctggtacagg cctctttttct tccctgaggc ccatgacatt tctctgttac tctagagggt    300
ttctcagatg gccagtaggc tcctccctgc ttagggtctc atttctctga aaagaggatg    360
aactgaaaag caggtagttc cagaagctaa ttgctgcttt ccatcataat tattttttctt    420 gtgagaacat ttctctttta attagctagt gatttgatt aagactaatt cactaaacat      480
aaccttccct caaatcacct caggtagcaa tctgtacgta actaaaag                 528

<210> SEQ ID NO 19
<211> LENGTH: 683
<212> TYPE: DNA
<213> ORGANISM: Homo sapiens
<220> FEATURE:
<221> NAME/KEY: misc_feature
<223> OTHER INFORMATION: Incyte ID No: 6749637H1

<400> SEQUENCE: 19
tgaatgaatt aggtgacacc tatagaagag ctatgacgtc gcatgcacgc gtacgtaagg     60
ctcggaattc ggctcgagaa agcaggtagt tccagaagct aattgctgct ttccatcata   120 attattttc ttgtgagaac atttctcttt taattagcta gtgattttga ttaagactaa     180
ttcactaaac ataccettcc ctcaaatcac ctcaggtagc aatctgtaag taactaaaag    240
cattgaaaaa cacacaagaa acatttttaa aaactatttt taaaggcctg gccgggtgca     300
gtggctcact cctgtaatcc cagcactttg ggaggccgag acgggtggat cacctgaggt    360
caggaatttg agactagcat ggccaacatg gtgaaacccc gtgtctacta aaaatacaaa    420
aattagctgg gcgtggtggc agacgcctgt aatcccagct actcagggag gctgaggcac    480
gagaatcgct tgaacctggg aggcggaggt tgcagtgagc caagattgcg ccactgcact    540
ccaacctggg tgacaagagc aagactccgt ctcacaaaaa acaaacaaaa ctgactgatt    600
gaatatacta aaccaaacta aaatcatatt cttttgatta agtttatcca tggctgtatt    660
cttctatgaa ttcttccatt taa                                            683

<210> SEQ ID NO 20
<211> LENGTH: 339
<212> TYPE: DNA
<213> ORGANISM: Homo sapiens
<220> FEATURE:
```

<221> NAME/KEY: misc_feature
<223> OTHER INFORMATION: Incyte ID No: 5073165F8

<400> SEQUENCE: 20

| | | | | | |
|---|---|---|---|---|---|
| ccaaactaaa | atcatattct | tttgattaag | tttatccatg | gctgtattct | tctatgaatt | 60 |
| cttccattta | attcttccac | gattatcttc | tcctgtaaat | acatcacagg | agttagaatt | 120 |
| ctctacccat | cagctgtacc | atgtcgcaga | attcatgcag | gcacaaagtt | ggagttacag | 180 |
| agatgggttg | acagcaggca | aactttggcc | tatgtattat | aaccacaact | tcaagttctt | 240 |
| acctcatgtg | aatattcacc | ctttctttag | tcttccaagg | caaacagccc | cgtctcatca | 300 |
| ccagatgagc | aaggtcttga | tatggcatag | cagatctcc | | | 339 |

<210> SEQ ID NO 21
<211> LENGTH: 494
<212> TYPE: DNA
<213> ORGANISM: Homo sapiens
<220> FEATURE:
<221> NAME/KEY: misc_feature
<223> OTHER INFORMATION: Incyte ID No: 6441214H1

<400> SEQUENCE: 21

| | | | | | |
|---|---|---|---|---|---|
| tctacccatc | agctgtacca | tgtcgcagaa | ttcatgcagg | cacaaagttg | gagttacaga | 60 |
| gatgggttga | cagcaggcaa | acttggccta | tgtattataa | ccacaacttc | aagttcttac | 120 |
| ctcatgtgaa | tattcaccct | ttctttagtc | ttccaaggca | aacagcccg | tctcatcacc | 180 |
| agatgagcaa | ggtcttgata | tggcatagca | gatctcccta | gacacagatc | atgagaaaag | 240 |
| atggaagaga | cttagggatt | caggcatcag | atgaagttgg | cttttccctt | ttatgccttg | 300 |
| tttgtattta | ccctgtctaa | tacactaagg | atacttactc | attgtacttg | cagctcaata | 360 |
| tgtctttgct | gttcagatac | taaaatgtac | ctctgagtca | ttgtgagctg | tgtggtaggt | 420 |
| tggacattgg | catagttggt | gatgggactc | aaaatgaaaa | ggtggtctct | ttaccaggtc | 480 |
| acagactgtt | gcag | | | | | 494 |

<210> SEQ ID NO 22
<211> LENGTH: 226
<212> TYPE: DNA
<213> ORGANISM: Homo sapiens
<220> FEATURE:
<221> NAME/KEY: misc_feature
<223> OTHER INFORMATION: Incyte ID No: 2436362H1
<221> NAME/KEY: unsure
<222> LOCATION: 222
<223> OTHER INFORMATION: a, t, c, g, or other

<400> SEQUENCE: 22

| | | | | | |
|---|---|---|---|---|---|
| gaacagtttt | acagaagtat | agtgcagatc | ccttaatgat | cctatcatcc | cagtttcaca | 60 |
| ctggaagaaa | ctgaggctca | gagattgagg | aaccttgtga | ctgccatctg | tgccagtcac | 120 |
| cacctctgca | tgaccacatt | tccctccatt | agcactacca | gcatgcctgt | gaggtagtta | 180 |
| ctcagctgtt | catctgaccc | cagacgtaga | aaagttaaga | gngatt | | 226 |

<210> SEQ ID NO 23
<211> LENGTH: 606
<212> TYPE: DNA
<213> ORGANISM: Rattus norvegicus
<220> FEATURE:
<221> NAME/KEY: misc_feature
<223> OTHER INFORMATION: Incyte ID No: 702073518T2

<400> SEQUENCE: 23

-continued

```
atctgatcat tctctgtagc cgaagagtgt ttggatgtgg tgaagggtct tggttcaagc      60
ccaaggttaa gatcttctta cttaaagcat ctattagctc gtacactttc tgcacttcca     120
ctcgaaggtc gttggcgtgc tccagactgt aggtcgtctc cccagcattt aatgatgctg     180
ccatcctgat gtattcagga gctttctgat caactttctc catgcaaagt cgaagtttct     240
cgtagagctt cacgatgtca ggcgtgtgct ccttctcatc catctgctgc tctctcttga     300
gcagcgtgtc cttgcagtgc gtgcagcagc ggatgcgctc atcatccttc tcgtccagga     360
ctgagctgac actgctcatg ctactgatgc tgcctcggcg ggagccatgg acactgttag     420
gtgactggct ggggctggtg tgggtgctca gggagtcctt gctggcactg gtgagcttat     480
ttgccaaggg caggccaatg agctccatac acttcttgca catgatagac ccacagaggc     540
ggcagtggtg acggcggttc cggatgctga acttattccc acagtctgga cagaatgaac     600
atctgg                                                                 606
```

<210> SEQ ID NO 24
<211> LENGTH: 556
<212> TYPE: DNA
<213> ORGANISM: Rattus norvegicus
<220> FEATURE:
<221> NAME/KEY: misc_feature
<223> OTHER INFORMATION: Incyte ID No: 702549617T1

<400> SEQUENCE: 24

```
gctatctgat cattctctgt agccgaagag tgtttggatg tggtgaaggg tcttggttca      60
agcccaaggt taagatcttc ttacttaaag catctattag ctcgtacact ttctgcactt     120
ccactcgaag gtcgttggcg tgctccagac tgtaggtcgt ctccccagtc atttaatgat     180
gctgccatcc tgatgtattc aggagctttc tgatcaactt tctccatgca agtcgaagt      240 ttctcgtaca gcttcacgat gtcaggcgtg tgctccttct catccatctg ctgctctctc     300
ttgagcagcg tgtccttgca gtgcgtgcag cagcggatgc gctcatcatc cttctcgtcc     360
aggactgagc tgacactgct catgctactg atgctgcctc ggcgggagcc atggacactg     420
ttaggtgact ggctggggct ggtgtgggtg ctcagggagt ccttgctggc actggtgagc     480
ttatttgcca aggcaggcc aatgagctcc atacacttct tgcacatgat agacccacag      540
aggcggcagt ggtgac                                                      556
```

<210> SEQ ID NO 25
<211> LENGTH: 452
<212> TYPE: DNA
<213> ORGANISM: Rattus norvegicus
<220> FEATURE:
<221> NAME/KEY: misc_feature
<223> OTHER INFORMATION: Incyte ID No: 702448734T1

<400> SEQUENCE: 25

```
tatctgatca ttctctgtag ccgaagagtg tttggatgtg gtgaagggtc ttggttcaag      60
cccaaggtta agatcttctt acttaaagca tctattagct cgtacacttt ctgcacttcc     120
actcgaaggt cgttggcgtg ctccagactg taggtcgtct ccccagcatt taatgatgct     180
gccatcctga tgtattcagg agctttctga tcaactttct ccatgcaaag tcgaagtttc     240
tcgtagagct tcacgatgtc aggcgtgtgc tccttctcat ccatctgctg ctctctcttg     300
agcagcgtgt ccttgcagtg cgtgcagcag cggatgcgct catcatcctt ctcgtccagg     360
actgagctga cactgctcat gctactgatg ctgcctcggc gggagccatg gacactgtta     420
ggtgactggc tggggctggt gtgggtgctc ag                                    452
```

<210> SEQ ID NO 26
<211> LENGTH: 567
<212> TYPE: DNA
<213> ORGANISM: Rattus norvegicus
<220> FEATURE:
<221> NAME/KEY: misc_feature
<223> OTHER INFORMATION: Incyte ID No: 702081830H1

<400> SEQUENCE: 26

| | | | | | |
|---|---|---|---|---|---|
| gtgctaagca | aggctccatt | ccattcttag | caccaaagag | ggaaaaaaag | taaaaagata | 60 |
| cctccattgt | cagctagtga | agaatcagcc | tcaccagcca | gatcatattc | accactgatt | 120 |
| cagaaaaaaa | cagcgaagag | tagcttactt | taatgatgct | gccatcctga | tgtattcagg | 180 |
| agctttctga | tcaactttct | ccatgcaaag | tcgaagtttc | tcgtagagct | tcacgatgtc | 240 |
| aggcgtgtgc | tccttctcat | ccatctgctg | ctctctcttg | agcagcgtgt | ccttgcagtg | 300 |
| cgtgcagcag | cggatgcgct | catcatcctt | ctcgtccagg | actgagctga | cactgctcat | 360 |
| gctactgatg | ctgcctcggc | gggagccatg | gacactgtta | ggtgactggc | tggggctggt | 420 |
| gtgggtgctc | agggagtcct | tgctggcact | ggtgagctta | tttgccaagg | gcaggccaat | 480 |
| gagctccata | cacttcttgc | acatgataga | cccacagagg | cggcagtggt | gacggcggtt | 540 |
| ccggatgctg | aacttattcc | cacagtc | | | | 567 |

<210> SEQ ID NO 27
<211> LENGTH: 383
<212> TYPE: DNA
<213> ORGANISM: Rattus norvegicus
<220> FEATURE:
<221> NAME/KEY: misc_feature
<223> OTHER INFORMATION: Incyte ID No: 702053775T1

<400> SEQUENCE: 27

| | | | | | |
|---|---|---|---|---|---|
| tgagtatctg | atcatctctg | tagccgaaga | gtgtgatgtg | gtgagggtct | ggtcagccca | 60 |
| gttagatctc | tacttaagca | tctattactc | tacactttct | gtgcttccct | ccgaaggtcg | 120 |
| ttggcgtgct | ccaaactgta | ggtcgtctcc | ccagcattta | atgatgctgc | catcctgatg | 180 |
| tattcaggag | ctttctgatc | aactttctcc | atgcaaagtc | gaagtttctc | gtagagcttc | 240 |
| acgatgtcag | gcgtgtgctc | cttctcatcc | atctgctgct | ctctcttgag | cagcgtgtcc | 300 |
| ttgcagtgcg | tgcagcagcg | gatgcgctca | tcatccttct | cgtccaggac | ttgagctgac | 360 |
| actgctcatg | ctactgatgc | tgc | | | | 383 |

<210> SEQ ID NO 28
<211> LENGTH: 255
<212> TYPE: DNA
<213> ORGANISM: Rattus norvegicus
<220> FEATURE:
<221> NAME/KEY: misc_feature
<223> OTHER INFORMATION: Incyte ID No: 700883909H1

<400> SEQUENCE: 28

| | | | | | |
|---|---|---|---|---|---|
| gttgatcctt | acatgtggga | acctcaagag | cttggtgcta | tgagaagcca | tctttctgat | 60 |
| tttaaaaaac | atcgtgctgc | aaggattgac | cactatgtta | ttgaagtcaa | taaattaata | 120 |
| atcaggttgg | aaaagcttac | cgcatttgac | agaacaaata | ctgagacctc | aaagattaga | 180 |
| gcaatagaaa | agtctgtggt | gccttgggtc | aatgaccagg | atgttccatt | ctgtccagac | 240 |
| tgtgggaata | agttc | | | | | 255 |

<210> SEQ ID NO 29
<211> LENGTH: 250
<212> TYPE: DNA
<213> ORGANISM: Rattus norvegicus
<220> FEATURE:
<221> NAME/KEY: misc_feature
<223> OTHER INFORMATION: Incyte ID No: 700883983H1

<400> SEQUENCE: 29

| | | | | |
|---|---|---|---|---|
| gttgatcctt | acatgtggga | acctcaagag | cttggtgcta | tgagaagcca | tctttctgat | 60 |
| tttaaaaaac | atcgtgctgc | aaggattgac | cactatgtta | ttgaagtcaa | taaattaata | 120 |
| atcaggttgg | aaaagcttac | cgcatttgac | agaacaaata | ctgagacctc | aaagattaga | 180 |
| gcaatagaaa | agtctgtggt | gccttgggtc | aatgaccagg | atgttccatt | ctgtccagac | 240 |
| tgtgggaata | | | | | 250 |

<210> SEQ ID NO 30
<211> LENGTH: 257
<212> TYPE: DNA
<213> ORGANISM: Rattus norvegicus
<220> FEATURE:
<221> NAME/KEY: misc_feature
<223> OTHER INFORMATION: Incyte ID No: 701092129H1

<400> SEQUENCE: 30

| | | | | | | |
|---|---|---|---|---|---|---|
| gtggtttggc | atctcataca | gccaatgggg | acatgaggtc | tcttcaaggc | atacctgccc | 60 |
| ccttgcgaaa | ggctgagggc | tggctcccac | tgtcagaagg | tcaggtacag | agtgaagacc | 120 |
| ccgaccctct | ccttcagcag | atctataaca | ttacatcgtt | catcaggcag | gccaaggctg | 180 |
| caggccgcac | agatgaggtg | cgcacacttc | aagagaacct | gcggcagctg | caagatgagt | 240 |
| atgaccagca | gcagact | | | | | 257 |

<210> SEQ ID NO 31
<211> LENGTH: 473
<212> TYPE: DNA
<213> ORGANISM: Rattus norvegicus
<220> FEATURE:
<221> NAME/KEY: misc_feature
<223> OTHER INFORMATION: Incyte ID No: 702137890H2

<400> SEQUENCE: 31

| | | | | | | |
|---|---|---|---|---|---|---|
| ctatggctgc | cgcgggtctc | tgaggaatct | cgaaggccgg | gagtcgggag | ctggagctgg | 60 |
| agagtaggct | gccggctgac | tgtcggaagt | cgcaggagga | gaggaagggt | gttggcttgc | 120 |
| tcggagccgc | caccgagagc | gcagcggtgg | ctgagattcc | ttctgctgaa | gagaggaaag | 180 |
| ctcatccaag | gccacaatgt | cacttcccag | ttatccaaga | gctgcttgct | caagctaaca | 240 |
| ctgccagaat | cctgctccct | tgggaggagt | caagctgact | tggcatgagg | tccctgcctt | 300 |
| cctggggttg | agagaagtac | aactatggca | tctttggatg | acgcagggga | agtgagggaa | 360 |
| ggcttcctgt | gccctctgtg | cctcaaggac | cttcagtctt | tctatcaact | tcagtcacat | 420 |
| tatgaggaag | aacactcagg | agatcgtgat | gtcaaagggc | aaattaaaaa | tct | 473 |

<210> SEQ ID NO 32
<211> LENGTH: 433
<212> TYPE: DNA
<213> ORGANISM: Macaca fascicularis
<220> FEATURE:
<221> NAME/KEY: misc_feature
<223> OTHER INFORMATION: Incyte ID No: 701741076T1

<400> SEQUENCE: 32

-continued

| | |
|---|---|
| caaagtgaca gtcactgtca gataacaagc acaatctgct acagtctgtg acctggtaaa | 60 |
| gagaacacct tttcatttgt gagtcccatc accaactatg acgatgtaca acctactgca | 120 |
| cagctcacaa tgactcagag atacatttta gtatctgaac agcaaagaca tattgagctg | 180 |
| ccagtacaat gagtaagtat ccttagtgta ttagacaggg ggaaatacaa acaaggcata | 240 |
| aaagggaaac gccaacttca tctgatgcct gactccctaa gtctcttcca tcttttctca | 300 |
| tgatctgtgt ctagggagat ctgctatgcc gtatcacgac cttgctcatt tggtgatgag | 360 |
| atggggctat ttgccttgga agactaacgg aagggtgaat attcacatga ggtaagaact | 420 |
| tgaagttgtg gtt | 433 |

<210> SEQ ID NO 33
<211> LENGTH: 645
<212> TYPE: DNA
<213> ORGANISM: Canis familiaris
<220> FEATURE:
<221> NAME/KEY: misc_feature
<223> OTHER INFORMATION: Incyte ID No: 702769948H2
<221> NAME/KEY: unsure
<222> LOCATION: 562
<223> OTHER INFORMATION: a, t, c, g, or other

<400> SEQUENCE: 33

| | |
|---|---|
| tgagtcttca ctctgcccct gacttcctga caacgggagc cagccctcag cttttctcag | 60 |
| ggagagcagg tcccctcga agggacacta cctccccgtt ggccgcatga gatgcgaggt | 120 |
| cactccgcct ttcctcaagc cgtcgttggg attctaggac agcctgtctc tccaggatcc | 180 |
| tcttcctctc catttcctgc ttccttttct ttttcagttc ctcaaactgt tctctggttg | 240 |
| gcaatgacat taaccccagc aacttttcct gcacaaaaag tgtagctgag tatctgatca | 300 |
| tcttctgtag ccgcaaggta tttggatgtg gtggagggtc ctggttcaag cctaaggtta | 360 |
| agatcttctt acttaaagca tctatgagct cgtacacttt ctgcacttcc actcgaaggt | 420 |
| caccagcatg ttccagactg taagttgttt ccccagcact aaggaaaaat catggaaata | 480 |
| ttcaagtttc atcaggatgc ctggggagta ttgtggaaaa gggttctaag ggtttagggc | 540 |
| cttacaaagg gagacacagc tnattttctc caagtagtat atttcacact cctgtataca | 600 |
| atgcaggact catttttttt ctaaatataa gtgctataat caggg | 645 |

<210> SEQ ID NO 34
<211> LENGTH: 542
<212> TYPE: DNA
<213> ORGANISM: Canis familiaris
<220> FEATURE:
<221> NAME/KEY: misc_feature
<223> OTHER INFORMATION: Incyte ID No: 702245053H1

<400> SEQUENCE: 34

| | |
|---|---|
| cctgaaccta actctggtct gacagaagtc tgtccccatt aggctgtggg ttctttcacc | 60 |
| tggggcttcc tctgccctgc tgggtacatc acacctgtgc agcagagggg ggagggggg | 120 |
| ttattgccct gaaggcaata gtttaggccc aggagagcct agcagctctt tttaagcagg | 180 |
| ggaggagggg gtgatgtttt accagggcat ttccctattg gtttaagtcc ttttttgtct | 240 |
| ctttcaggaa gttaaacttc cagtgcaggc gtatcactgg gtctgaccac aggctgttta | 300 |
| gaaaatagga gtggtgacct ttttggttga tggaggcagt agtatttggg agaagaatct | 360 |
| ctacccaaat gttcctctga atgatggaac aatttgtccc cagagaaacc tccctctaga | 420 |
| attttggtga aaataccctg atctgggctt tttcagaggg tccaggctat aatttaggat | 480 |

| tggtaatcag gaagcttttg tggaacactg ccatgggagt ggaagcttcc ttgagtcaga | 540 |
| ag | 542 |

<210> SEQ ID NO 35
<211> LENGTH: 281
<212> TYPE: DNA
<213> ORGANISM: Homo sapiens
<220> FEATURE:
<221> NAME/KEY: misc_feature
<223> OTHER INFORMATION: Incyte ID No: g921283

<400> SEQUENCE: 35

| gaacttcaag ttcttacctc atgtgaatat tcaccctttc tttagtcttc caaggcaaac | 60 |
| agccccgtct catcaccaga tgagcaaggt cttgatatgg catagcagat ctccctagac | 120 |
| acagatcatg agaaaagatg gaagagactt agggattcag gcatcagatg aagttggctt | 180 |
| ttccctttta tgccttgttt gtatttaccc tgtctaatac actaaggata cttactcatt | 240 |
| gtacttgcag ctcaatatgt ctttgctgtt cagatactaa a | 281 |

<210> SEQ ID NO 36
<211> LENGTH: 6719
<212> TYPE: DNA
<213> ORGANISM: Homo sapiens
<220> FEATURE:
<221> NAME/KEY: misc_feature
<223> OTHER INFORMATION: Incyte ID No: GNFL.g8572864_000002_002.edit

<400> SEQUENCE: 36

| aaattacgac tttgcatgga gaaagttgac cagaaagctc cagaatacat caggatggca | 60 |
| gcatcattaa atgctgggga gacaacctac agtctggaac atgccagtga ccttcgagtg | 120 |
| gaagtgcaga aagtgtatga gctgatagac gctttaagta agaagatctt aaccttgggc | 180 |
| ttgaaccagg accctccacc acatccaagc aatttgcggc tgcagagaat gatcagatac | 240 |
| tcagctacac tttttgtgca ggaaaagttg cttggtttga tgtcactgcc aaccaaagaa | 300 |
| cagtttgagg aactgaaaaa gaaaggaag gaggaaatgg agaggaagag ggccgtggag | 360 |
| agacaagctg ccctggagtc ccagcgaagg cttgaggaaa ggcagagtgg cctggcttct | 420 |
| cgagcggcca acggggaggt ggcatctctc cgcaggggcc ctgcccctt gagaaaggct | 480 |
| gagggctggc tcccactgtc aggaggtcag gggcagagtg aggactcaga cccgctcctc | 540 |
| cagcagatcc acaacatcac atcattcatc aggcaggcca aggccgcggg ccgcatggat | 600 |
| gaagtgcgca ctctgcagga aacctgcgg cagctgcagg acgagtatga ccagcagcag | 660 |
| acagagaagg ccatcgagct gtcccggagg caggctgagg aggaggacct gcagcgggaa | 720 |
| cagctgcaga tgttgcgtga acgggagttg gaacgagaaa gggagcagtt tcgggtggca | 780 |
| tccctgcaca cacggactcg gtccctggac ttcagagaaa tcggccctt tcagctggag | 840 |
| cccagcagag agcctcgcac ccaccttgct tatgctttgg atctaggctc ttccccagtt | 900 |
| ccaagcagca cagctcccaa gaccccttca cttagctcaa ctcaacccac cagagtgtgg | 960 |
| tctgggcccc cagccgttgg ccaggagcgc ttaccccaga gcagcatgcc acagcaacat | 1020 |
| gaggggccct ccttaaaccc ctttgatgag gaagacctct ccagccccat ggaagaggcc | 1080 |
| actactggtc tcctgctgc aggggttcc ttagacccct cagcccgcat cctgaaagag | 1140 |
| tacaatcctt tcgaggaaga ggacgaggag gaggaagcag tggcagggaa tccattcatt | 1200 |
| cagccagaca gcccagctcc taaccccttc agtgaggaag acgaacatcc ccagcagagg | 1260 |
| ctctcaagcc ctctggttcc tggtaacccc tttgaggaac ccacctgtat caaccccttt | 1320 |

```
gagatggaca gtgacagtgg gccagaggct gaggagccca tagaggaaga gctcctcctg    1380
cagcagatcg ataacatcaa ggcatacatc tttgatgcca agcagtgcgg ccgcctggat    1440
gaggtagagg tgctgacaga gaatctgcgg gagctgaagc acaccctggc caagcagaag    1500
gggggcactg actgaccagc agtggagagg gcacctttgg gcccaggggt ctggcaggag    1560
ccagtggagc aggacagagg gcaggcagga tggatgggga aggtggcagg gtgagaactc    1620
agatgcacac aggtgagggg caggaatctg ctgttttgtg ttgcgcactt tgaggtattt    1680
ccactacagt tgaataataa aatagaaact agaacaggga gaatcagcat tcagttgctg    1740
cttttcctgt ttattattac tatcttttgt aatcggaggt ttaccccttt tgaagggact    1800
ttacattttt actaccgaga tataactaaa tgcagctctg ttgggcccag ggcagaaatg    1860
gctgctgtgt acctcttggg tccatttgct actgcctagt cttggttcct tatgcagtat    1920
tatagggcag cctttttaga gcccttcctt tagccaagac agagaagata gattccactg    1980
agctctattc tgctctgaca gaagtccatc cctagtaggc tgtgagttcc atttcacctg    2040
gggccgcctc tccctgctc tgcacttcct gtctgtacaa tagaagggg aggtgctgct    2100 atgaagggga gagtttagac ccaggagagc ccagcacctc tttttaaggt ggggtgatgg    2160
gaatatttca ccaggtctat ttttctcagt ttaagttctt ttttgtctct ttcaggaagt    2220
taagctccca gtgcaggta tcaatgtgaa tctggtcctg agcttttag aaaataagag    2280 tggtggccgg gcgcgctggc tcacgcctgt aatcgcaaca ctttgggagg ccgaggcagg    2340
cagatcacaa ggtcaggaga tcgagaccac cctggctaac acagtgaaat cccgtctcta    2400
ctaaaaatac aaaaaattag ccaggcgtgg tggtgggtgc ctgtagtccc agctactttg    2460
gaggctgagg caggagaatg ctgtgaaccc gggaggcaga gcttgcagtg agccgagatc    2520
gcaccactgc actccagcct gggcagtgag agtgagactc cgtctcaaaa aaaaataaga    2580
gtggttaact ttttggttga tattagtatt atttgtgaga agagtttccc caccttctt    2640 ctgatagaac aattgtctgt cactggagaa atctccctcc agagctttgg caaagttact    2700
ctgatctggg tctgtttaaa aggccgggtc tctaatttag gaatcggtga tttggaagct    2760
tttgcagaac atcaccagaa gaagggaagc ttcccagagt cagaagctaa attaaaataa    2820
tttccaaggc tatttgatca gccttcttcc ttttggttc attgtgtcct gacttggggc    2880
actgatgaga tttttttattt ttttttgagac agagtttcac tttgttgccc aggctggagt    2940
gtagtggcat gatctcagct cactgcaacc tccacctccc tggttcaagt gatatttgtg    3000
cctcagcccc ctgaatagct aggattacag gcgtgggcca ccacgcctgg ttaatctctg    3060 tattttagt agaggtagag tttcaccatt ttggccaggc tggtttcgaa ctcctggcct    3120
caagtgatct gccaccttgg cctcccaaag tgctgggaat acaggcgtga gccactgtgc    3180
ccgccctgat gagatatttt attaccaatg ttagtattga gaaactgaaa tgtttgaaga    3240
agcacaaccc aggatcgtgc tggtagcacc acagtactta aactgttggt caattaaggc    3300
cagaaaggga aattgttaat ttagctctga gagctttaag tttacaggaa cataactctt    3360
aactgacatc tgcatcatg atagccatat gtgctcagct ctgcggtaga gtttctgcag    3420
ttactcatct gaactaatga acaataactg accactagtc actttatgcc gtgtaactag    3480
ctctaggcca tactttcact ggttactggt gtgaaagctg aaattcattt tgttacattc    3540
tggtgaagac ccctccttgat aatgggaatg ttttaactct cttgatgaaa aaataatctg    3600
tatttgtgtt gatgttcaca tttctgtagc acatttctta tccttttggt tgaatgaaaa    3660
```

-continued

```
gatcttgtat agggtgtgg agatggggag tgggtagaag tgtgtgaagg acgctttgca    3720
tttgggatct gttcacaaac agccatatga gtgtgttaat gaatgtcagc cagttaccaa    3780
ccctgctggt tgttatgggt tgttttgaga agttggcaac caggcatcta agatgttgcc    3840
tggtacaggc ctcttttctt ccctgaggcc catgacattt ctctgttact ctagagggtt    3900
tctcagatgg ccagtaggct cctccctgct tagggtctca tttctctgaa aagaggatga    3960
actgaaaagc aggtagttcc agaagctaat tgctgctttc catcataatt attttcttg    4020
tgagaacatt tctcttttaa ttagctagtg attttgatta agactaattc actaaacata    4080
cccttccctc aaatcacctc aggtagcaat ctgtaagtaa ctaaaagcat tgaaaaacac    4140
acaagaaaca ttttaaaaa ctattttaa aggcctggcc gggtgcagtg gctcactcct    4200
gtaatcccag cactttggga ggccgagacg ggtggatcac ctgaggtcag gaatttgaga    4260
ctagcatggc caacatggtg aaaccccgtg tctactaaaa atacaaaaat tagctgggcg    4320
tggtggcaga cgcctgtaat cccagctact cagggaggct gaggcacgag aatcgcttga    4380
acctgggagg cggaggttgc agtgagccaa gattgcgcca ctgcactcca acctgggtga    4440
caagagcaag actccgtctc acaaaaaaca aacaaaactg actgattgaa tatactaaac    4500
caaactaaaa tcatattctt ttgattaagt ttatccatgg ctgtattctt ctatgaattc    4560
ttccatttaa ttcttccacg attatcttct cctgtaaata catcacagga gttagaattc    4620
tctacccatc agctgtacca tgtcgcagaa ttcatgcagg cacaaagttg gagttacaga    4680
gatgggttga cagcaggcaa acttggccta tgtattataa ccacaacttc aagttcttac    4740
ctcatgtgaa tattcaccct ttctttagtc ttccaaggca aacagccccg tctcatcacc    4800
agatgagcaa ggtcttgata tggcatagca gatctcccta gacacagatc atgagaaaag    4860
atggaagaga cttagggatt caggcatcag atgaagttgg cttttccctt ttatgccttg    4920
tttgtattta ccctgtctaa tacactaagg atacttactc attgtacttg cagctcaata    4980
tgtctttgct gttcagatac taaaatgtac ctctgagtca ttgtgagctg tgtggtaggt    5040
tggacattgg catagttggt gatgggactc aaaatgaaaa ggtggtctct ttaccaggtc    5100
acagactgta gcagattgtg cttgttatct gacaatgact gtcactttga ggtcgttga    5160
tttgcatgca ctactctggg gccttgtatt ggagcctttt ttaaaaaaaa taaaatctga    5220
gatagaggtt gggggtgtgt gtgtctgtgt gcacatgtgt tacaagtgag aatcatcaga    5280
tgacatccct tctcctttct tgatgacaac catctgagta tcagaatagt tccagcacct    5340
gtgttgtttg tctggttaag gcctctggaa aaaatgaagg tcactgggtt ctgaacaggg    5400
gatagatacg ggttccagtt ctgcccttat tcccagttat tcctgcagtg ctggttaaat    5460
gaacagtttt acagaagtat agtgcagatc ccttaatgat cctatcatcc cagtttcaca    5520
ctggaagaaa ctgaggctca gagattgagg aaccttgtga ctgccatctg tgccagtcac    5580
cacctctgca tgaccacatt tccctccatt agcactacca gcatgcctgt gaggtagtta    5640
ctcagctgtt catctgaccc cagacgtaga aaagttaaga gagattagcc tggcttaggc    5700
cacacagcca gtcagtggtg gaatgagggt ttaaatccag atctgcctga cttaatttgc    5760
cctcagtaat aagtagctgg gtcaggtagt ggtgtggtgg tggtgggtgc tcaaccattg    5820
tgtcaagctc aaagagggca gaaagggca atggggaatg aggttgggtg ctgctgagct    5880
ggtttccgat agtgactgcc tgagtctgtg aaactgagac ctccttaggg ccttaagaat    5940
atatagattc ttaaaccagg agagtataat atctagtgct cactgtaggc tagactgagt    6000
gctaagtatt acgcatggct tacctcagtc ttcccaacaa cccatttaca catgcagaaa    6060
```

```
tgagtgagtg gtgaagttaa gcttgcttag ggttgcactg ctgggtttcc agcctaggtc    6120
tgtctgactg caaaacccaa gctgccctag attgtgttgt atgtggacac ccatgtttct    6180
aatgtggaat ggggtgtttc atccctagca agtgcctcct gtggactttt aagatgaaaa    6240
acttctgcct aactcttcag gaagcctagc gtagttgtaa aaatacttca gaaagcactt    6300
ctggttttag ctcagacacg tagagtttga aagttatcct atccttacca caagaaaaag    6360
ctgggcaaac tcaaaagcat tggcctttct tggtcccatt agagagctga gtgtgcaggt    6420
caaactgcca tcccaaaatc tagagagagg tgagtccaga gagtgagcaa gatctaattg    6480
cctggagcag aagccacggg agccatagct agtaggaaaa cttaaatggt aattttgatg    6540
aactgctgga ggttgagtgt ggactagcat gggagggagc aactccccct cacccccaac    6600
gctttcctgg gttttaccct acttggttct attggtgaag agctgaggaa gaccctctgg    6660
tgactctggc aggggaaagg gagaatcatc tttgtaatca gagccttctc cataataaa     6719
```